United States Patent
Pfannenstiel et al.

(10) Patent No.: US 12,023,093 B2
(45) Date of Patent: Jul. 2, 2024

(54) BRONCHOSCOPIC-BASED MICROWAVE ABLATION SYSTEM AND METHOD

(71) Applicants: Broncus Medical Inc., San Jose, CA (US); Kansas State University Research Foundation, Manhattan, KS (US)

(72) Inventors: Austin Pfannenstiel, Manhattan, KS (US); Thomas M Keast, Sunnyvale, CA (US); Henky Wibowo, San Jose, CA (US); Punit Prakash, Manhattan, KS (US)

(73) Assignees: Broncus Medical Inc., San Jose, CA (US); Kansas State University Research Foundation, Manhattan, KS (US)

( * ) Notice: Subject to any disclaimer, the term of this patent is extended or adjusted under 35 U.S.C. 154(b) by 503 days.

(21) Appl. No.: 16/478,841

(22) PCT Filed: Jan. 26, 2018

(86) PCT No.: PCT/US2018/015584
§ 371 (c)(1),
(2) Date: Jul. 17, 2019

(87) PCT Pub. No.: WO2018/140816
PCT Pub. Date: Aug. 2, 2018

(65) Prior Publication Data
US 2020/0054396 A1     Feb. 20, 2020

Related U.S. Application Data

(60) Provisional application No. 62/450,916, filed on Jan. 26, 2017.

(51) Int. Cl.
*A61B 18/18*     (2006.01)
*A61B 1/018*     (2006.01)
(Continued)

(52) U.S. Cl.
CPC .......... *A61B 18/1815* (2013.01); *A61B 1/018* (2013.01); *A61B 1/2676* (2013.01);
(Continued)

(58) Field of Classification Search
CPC ...... A61B 18/1815; A61B 2018/00023; A61B 18/00541; A61B 18/00577;
(Continued)

(56) References Cited

U.S. PATENT DOCUMENTS 7,311,703 B2 *  12/2007  Turovskiy .......... A61B 18/1815
                                                                606/33
2004/0133254 A1   7/2004  Sterzer et al.
(Continued)

FOREIGN PATENT DOCUMENTS

| CN | 110494093 A | 9/2019 | |
| EP | 3573561 A1 | 12/2019 | |
| WO | WO-2016197206 A1 * | 12/2016 | ......... A61B 18/1815 |

OTHER PUBLICATIONS

C. L. Brace, T. A. Diaz, J. L. Hinshaw, and F. T. Lee, "Tissue contraction caused by radiofrequency and microwave ablation: a laboratory study in liver and lung," J. Vasc. Interv. Radiol. JVIR, vol. 21, No. 8, pp. 1280-1286, Aug. 2010.
(Continued)

*Primary Examiner* — Khadijeh A Vahdat
*Assistant Examiner* — Marina Delaney Templeton
(74) *Attorney, Agent, or Firm* — Batt IP A Law Corporation; Richard Batt

(57) ABSTRACT

A novel microwave ablation applicator includes a flexible tubular shaft and a partially encapsulated antenna. The applicator is adapted to be used with an endoscope in order to access remote targets deep within an organ of a patient. Microwave power is emitted from the antenna in a desired radiation pattern by circulating an attenuating liquid through (Continued)

the shaft and across a portion of the antenna. Microwave ablation systems and methods are described.

20 Claims, 14 Drawing Sheets

(51) Int. Cl.
*A61B 1/267* (2006.01)
*A61B 18/00* (2006.01)

(52) U.S. Cl.
CPC ............ *A61B 2018/00023* (2013.01); *A61B 2018/00541* (2013.01); *A61B 2018/00577* (2013.01); *A61B 2018/00642* (2013.01); *A61B 2018/00785* (2013.01); *A61B 2018/00791* (2013.01); *A61B 2018/00982* (2013.01); *A61B 2018/1823* (2013.01); *A61B 2018/1838* (2013.01); *A61B 2018/1853* (2013.01); *A61B 2018/1861* (2013.01)

(58) Field of Classification Search
CPC ........ A61B 18/00642; A61B 18/00791; A61B 18/1823; A61B 18/1853; A61B 18/1861; A61B 18/00005; A61B 18/00011; A61B 18/1838; A61B 18/00785; A61B 18/1884; A61B 18/1892; A61B 18/1846
See application file for complete search history.

(56) References Cited

U.S. PATENT DOCUMENTS

| | | |
|---|---|---|
| 2007/0203551 A1 | 8/2007 | Cronin et al. |
| 2008/0275436 A1* | 11/2008 | Cronin ............... A61B 18/18 606/33 |
| 2008/0294162 A1* | 11/2008 | Rossetto ............... A61B 18/14 606/50 |
| 2009/0082762 A1* | 3/2009 | Ormsby ............ A61B 18/1815 606/33 |
| 2009/0187186 A1 | 7/2009 | Jakus |
| 2009/0222002 A1* | 9/2009 | Bonn ............... A61B 18/1815 606/33 |
| 2010/0145328 A1* | 6/2010 | Hancock ............ A61B 18/1815 606/33 |
| 2011/0077635 A1* | 3/2011 | Bonn ................. H01Q 9/16 343/906 |
| 2011/0152853 A1 | 6/2011 | Manley et al. |
| 2012/0172860 A1* | 7/2012 | Brannan ............ A61B 18/1815 606/33 |
| 2012/0172862 A1* | 7/2012 | Brannan ............... A61B 18/18 606/33 |
| 2013/0267943 A1 | 10/2013 | Hancock |
| 2014/0046174 A1 | 2/2014 | Ladtkow et al. |
| 2014/0046175 A1 | 2/2014 | Ladtkow et al. |
| 2014/0046316 A1* | 2/2014 | Ladtkow ................ A61B 1/018 606/33 |
| 2014/0081254 A1* | 3/2014 | Rudie ................. A61B 18/1815 606/27 |
| 2014/0259641 A1 | 9/2014 | Brannan et al. |
| 2014/0276739 A1 | 9/2014 | Brannan et al. |
| 2014/0276740 A1 | 9/2014 | Larson et al. |
| 2016/0030112 A1 | 2/2016 | Brannan et al. |
| 2016/0058507 A1* | 3/2016 | Dickhans ............... A61B 90/39 606/33 |
| 2016/0058508 A1* | 3/2016 | Brannan ............... A61B 18/14 606/33 |
| 2016/0095657 A1 | 4/2016 | Brannan |
| 2016/0296281 A1 | 10/2016 | Bonn |
| 2017/0196639 A1 | 7/2017 | Liao |
| 2017/0265940 A1 | 9/2017 | Prakash et al. |
| 2019/0069951 A1* | 3/2019 | Hancock ........... A61B 18/1492 |
| 2020/0054396 A1 | 2/2020 | Pfannenstiel et al. |

OTHER PUBLICATIONS

D. H. Sterman et al., "High yield of bronchoscopic transparenchymal nodule access real-time image-guided sampling in a novel model of small pulmonary nodules in canines," Chest, vol. 147, No. 3, pp. 700-707, Mar. 2015.

Dewey, "Arrhenius relationships from the molecule and cell to the clinic," Int. J. Hyperthermia, vol. 25, No. 1, pp. 3-20, Jan. 2009.

G. Deshazer, D. Merck, M. Hagmann, D. E. Dupuy, and P. Prakash, "Physical modeling of microwave ablation zone clinical margin variance," Med. Phys., vol. 43, No. 4, p. 1764, Apr. 2016.

International Preliminary Report on Patentability of the counterpart International Application PCT/US2018/015584 issued on Jul. 30, 2019.

International Search Report of the counterpart International Application PCT/US2018/015584 issued on Apr. 13, 2018.

J. Sebek, N. Albin, R. Bortel, B. Natarajan, and P. Prakash, "Sensitivity of microwave ablation models to tissue biophysical properties: A first step toward probabilistic modeling and treatment planning," Med. Phys., vol. 43, No. 5, p. 2649, May 2016.

K. Harris, J. Puchalski, and D. Sterman, "Recent Advances in Bronchoscopic Treatment of Peripheral Lung Cancers," Chest, Mar. 2017.

R. C. Ward, T. T. Healey, and D. E. Dupuy, "Microwave ablation devices for interventional oncology," Expert Rev. Med. Devices, vol. 10, No. 2, pp. 225-238, Mar. 2013.

R. Eberhardt, N. Kahn, and F. J. F. Herth, "'Heat and destroy': bronchoscopic-guided therapy of peripheral lung esions," Respir. Int. Rev. Thorac. Dis., vol. 79, No. 4, pp. 265-273, 2010.

S. Curto, M. Taj-Eldin, D. Fairchild, and P. Prakash, "Microwave ablation at 915 MHz vs 2.45 GHz: A theoretical and experimental investigation," Med. Phys., vol. 42, No. 11, pp. 6152-6161, Nov. 2015.

Supplementary European Search Report of the counterpart EP application EP3573561 issued on Oct. 8, 2020.

T. J. Vogl, R. Eckert, N. N. N. Naguib, M. Beeres, T. Gruber-Rouh, and N.-E. A. Nour-Eldin, "Thermal Ablation of Colorectal Lung Metastases: Retrospective Comparison Among Laser-Induced Thermotherapy, Radiofrequency Ablation, and Microwave Ablation," Am. J. Roentgenol., pp. 1-10, Sep. 2016.

T. Kawai et al., "Creation of a tumor-mimic model using a muscle paste for radiofrequency ablation of the lung," Cardiovasc. Intervent. Radiol., vol. 32, No. 2, pp. 296-302, Mar. 2009.

Thomas P. Ryan, "Microwave Ablation for Cancer: Physics, Performance, Innovation, and the Future," in Image-Guided Cancer therapy, New York: Springer Science+Business Media, 2013.

\* cited by examiner

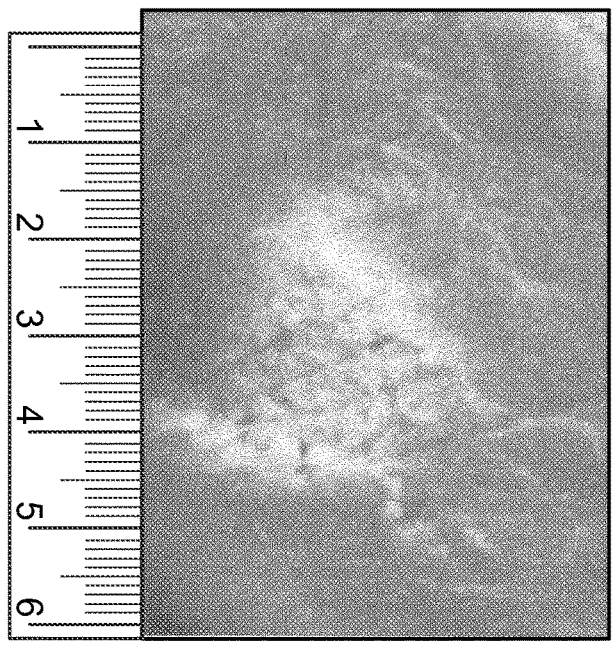
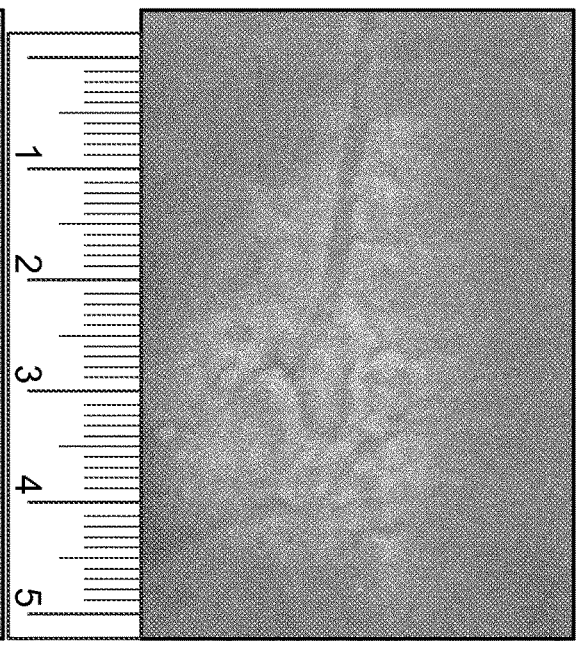
FIG. 13A             FIG. 13B
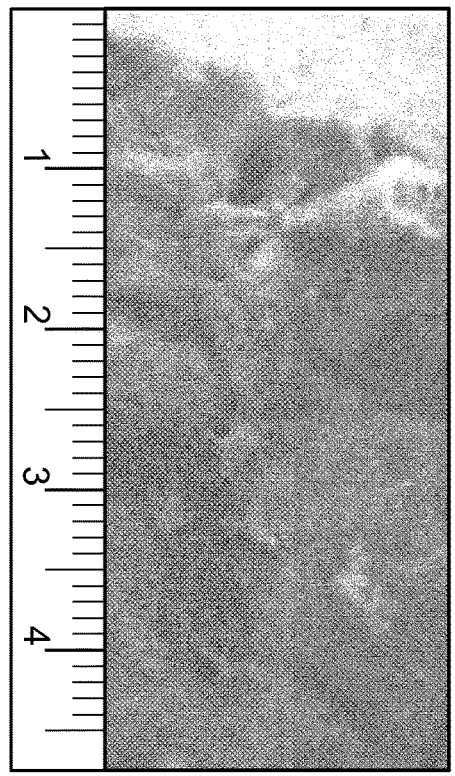
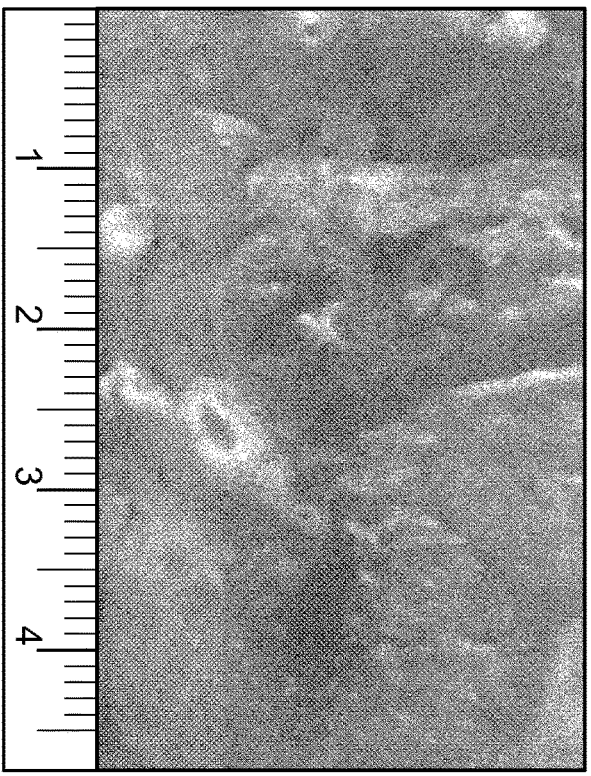
FIG. 14A             FIG. 14B

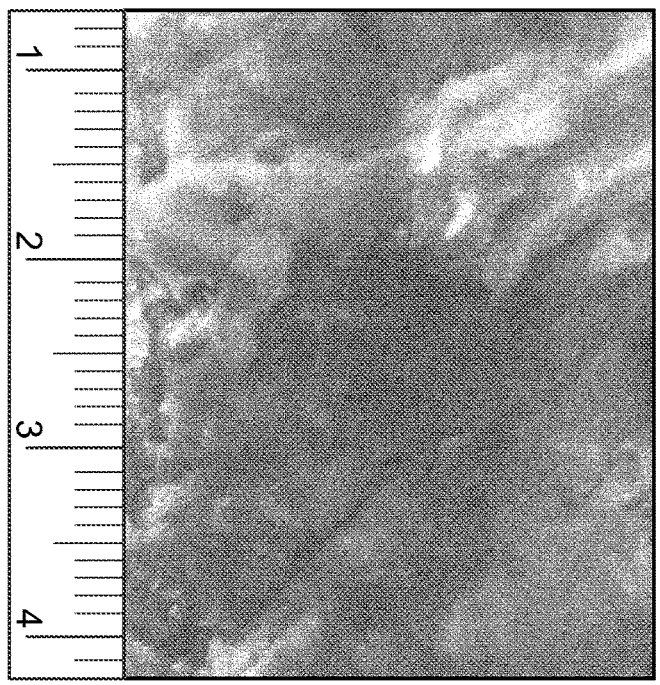 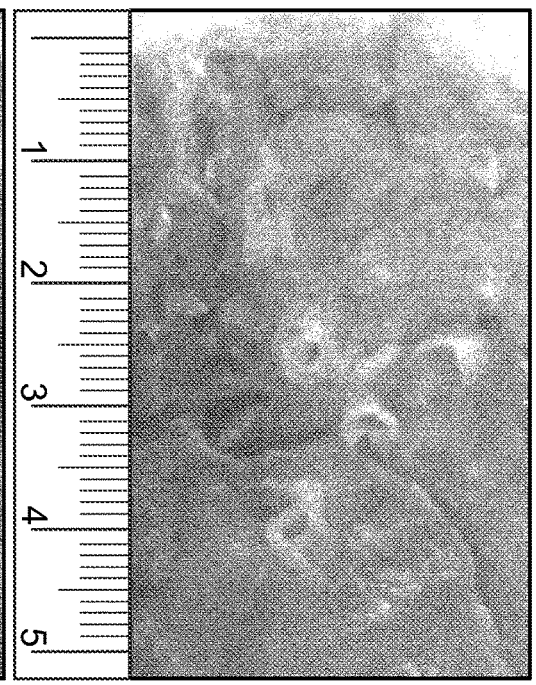
FIG. 15A                    FIG. 15B

BRONCHOSCOPIC-BASED MICROWAVE ABLATION SYSTEM AND METHOD

CROSS-REFERENCE TO RELATED APPLICATIONS

The present International PCT application claims the benefit of priority to U.S. Provisional Patent Application No. 62/450,916, filed Jan. 26, 2017.

TECHNICAL FIELD

The present invention relates to electrosurgical devices operable to deliver microwave energy of sufficient intensity to cause targeted ablation of tissue located within a human or animal body.

BACKGROUND ART

Microwave ablation (MWA) is one of several energy modalities in clinical use for thermal treatment of cancer. The goal of thermal ablation is heating of the target tissue to toxic temperatures, leading to cell death by coagulation necrosis. Thomas Ryan P., "Microwave Ablation for Cancer: Physics, Performance, Innovation, and the Future," in *Image-Guided Cancer therapy*, New York: Springer Science+Business Media, 2013. MWA is a minimally invasive procedure which can be used for unresectable tumors, or for patients who have complicated medical conditions that would prevent chemotherapy, radiotherapy, or traditional surgery. MWA procedures are typically performed with image guidance such as ultrasound or computed tomography (CT) to identify the disease, position the applicator, and confirm adequate treatment. G. Deshazer, D. Merck, M. Hagmann, D. E. Dupuy, and P. Prakash, "Physical modeling of microwave ablation zone clinical margin variance," *Med. Phys.*, vol. 43, no. 4, p. 1764, April 2016. MWA has shown less complication rates than surgical resection and therefore makes it a preferred option for high-risk patients not suited for more physically demanding or invasive treatments. Deshazer et al.

With reference to FIG. 1, MWA is typically performed by inserting a rigid, needle-like antenna applicator 10 into the target tumor 30 of a patient's lung 24 and applying energy supplied from a microwave generator. Common frequencies range from 915 MHz or 2.45 GHz, although systems operating at other frequencies are under consideration. S. Curto, M. Taj-Eldin, D. Fairchild, and P. Prakash, "Microwave ablation at 915 MHz vs 2.45 GHz: A theoretical and experimental investigation," *Med. Phys.*, vol. 42, no. 11, pp. 6152-6161, November 2015. Ideally, MWA procedures would ablate the tumor with an additional 5-10 mm margin along the entire tumor boundary 50 to account for any additional cancer cells undetected by imaging. See Deshazer et al. Heat is produced when the rapidly oscillating radiated electric field induces rotation of polar molecules in tissue (such as water) which attempt to align with the orientation of the applied field. Thermal damage induced in tissue is a function of the transient temperature profile during heating; coagulation necrosis occurs as tissue temperatures exceed ~55° C. W. C. Dewey, "Arrhenius relationships from the molecule and cell to the clinic," Int. J. Hyperthermia, vol. 25, no. 1, pp. 3-20, January 2009. The resulting size and shape (volume) of the treated area is determined by the antenna's radiating pattern, local heat conduction, and heat losses due to blood perfusion.

Although currently available percutaneous microwave ablation (MWA) systems for treating lung lesions have demonstrated improved local tumor control over other ablation modalities such as laser and radiofrequency ablation (e.g., 88% for MWA compared to 68% and 69% for laser and radiofrequency, respectively T. J. Vogl, R. Eckert, N. N. N. Naguib, M. Beeres, T. Gruber-Rouh, and N.-E. A. Nour-Eldin, "Thermal Ablation of Colorectal Lung Metastases: Retrospective Comparison Among Laser-Induced Thermotherapy, Radiofrequency Ablation, and Microwave Ablation," *Am. J. Roentgenol.*, pp. 1-10, September 2016.), percutaneous ablation comes with a high associated risk of disrupting the pleural membrane 25. Disrupting the pleural membrane can result in a pneumothorax: a very undesirable if not deadly complication. It follows that the range of lung tumors that can be accessed with a percutaneous approach are fundamentally limited by the location of the tumors and surrounding anatomy (heart, large blood vessels, diaphragm, ribs). With increased detection of peripheral nodules through low-dose CT screening, the number of patients with localized disease that can be treated with a minimally-invasive approach is expected to increase substantially. K. Harris, J. Puchalski, and D. Sterman, "Recent Advances in Bronchoscopic Treatment of Peripheral Lung Cancers," Chest, June 2016.

Thermal ablation of lung targets via a bronchoscopic approach has been proposed as a minimally invasive means for treatment of early-stage tumors. R. Eberhardt, N. Kahn, and F. J. F. Herth, "'Heat and destroy': bronchoscopic-guided therapy of peripheral lung lesions," Respir. Int. Rev. Thorac. Dis., vol. 79, no. 4, pp. 265-273, 2010. Advances in bronchoscopic guidance and navigation techniques are expected to increase the ability to deliver applicators to targeted tumors via bronchoscopes. D. H. Sterman et al., "High yield of bronchoscopic transparenchymal nodule access real-time image-guided sampling in a novel model of small pulmonary nodules in canines," Chest, vol. 147, no. 3, pp. 700-707, March 2015.

A challenge with MWA devices, however, is to work within the narrower and longer working lumens of bronchoscope. Bronchoscopic devices must be <2 mm in diameter to fit within working channels of available scopes, and ~1.5 m long to access targets in the peripheral lung.

Currently available percutaneous MWA devices range in size between 17 G (~1.5 mm) to 13 G (~2.4 mm) R. C. Ward, T. T. Healey, and D. E. Dupuy, "Microwave ablation devices for interventional oncology," Expert Rev. Med. Devices, vol. 10, no. 2, pp. 225-238, March 2013; percutaneous MWA applicators are typically ~15-30 cm in length. Smaller diameters necessitate the use of smaller and longer cables, which yield increased heating due to electromagnetic attenuation within coaxial cables. For example, UT-34 cable at 1.0 GHz has an attenuation coefficient of 1.58 dB/m. Considering 60 W applied power, a 20 cm cable for a percutaneous applicator will yield 2.2 W loss within the cable, compared to 14.3 W in a 1.5 m cable for a bronchoscopic applicator. This added cable heating undesirably risks thermal damage to the applicator, bronchoscope, and non-targeted tissue proximal to the applicator's active length.

Microwave ablation assemblies and techniques for heating and destroying tumor cells within a body are described in various patents, some of which describe use of ablation using flexible elongate members or catheters. Examples of these assemblies and techniques are described in U.S. Patent Application Publication Nos. 2017/0265940, 2016/0095657, 2014/0259641, and 2014/0276739.

Bronchoscopic and endoscopic delivery of microwaves is challenging because of the considerable attenuation within thin coaxial cables. A disadvantage is significant energy losses in connecting cables which may need to be compensated for by cooling. See Thomas, Ryan P. The microwave losses within the cables reduces energy delivered to tissue and leads to waste heating along the applicator that may result in unintended tissue heating, damage to the bronchoscopes/endoscopes, and/or degradation of device performance. Moreover, due to the size constraints of bronchoscope/endoscope working channels, conventional approaches for mitigating microwave ablation zone length (e.g. baluns or triaxial elements) which increase device diameter, are not acceptable.

Accordingly, there is still a need to address the above mentioned challenges associated with microwave ablation.

SUMMARY OF THE INVENTION

A novel flexible MWA applicator to treat pulmonary malignancies via a bronchoscope can improve treatment efficacy through increased applicator placement accuracy and improve safety by reducing the risk of common complications such as pneumothorax.

Embodiments of the present invention are directed to systems and methods for delivering microwaves at power levels that are required for hyperthermic treatment of human and animal tissues.

In embodiments of the invention, devices, systems and methods are directed to bronchoscopic/endoscopic delivery of microwaves as opposed to percutaneous delivery.

In embodiments of the invention, devices are constructed to have a relatively small diameter and relatively large length in order to access targets endoscopically.

Additionally, devices described herein are sufficiently flexible to be delivered to targeted tumors through the working channels of bronchoscopes. In embodiments of the invention, devices are constructed of a thin and flexible coaxial cable, with a bend radius suitable for reaching ablation targets via a bronchoscopic/endoscopic approach. In embodiments of the invention, devices are adapted to be able to transit a 180° bend radius of 1" or less. In embodiments, the bend radius is on the order of 2.5 cm, 2.0 cm, 1.5, cm, 1 cm, or less.

In embodiments of the invention, the devices have a sufficiently pre-set or biased shape such that once near the target, the devices may be advanced to exit the bronchoscope, penetrate the parenchyma, and accurately reach the tumor. In particular embodiments, the devices traverse along a straight path along the central axis of the target.

In embodiments of the invention, the devices are balunless, and thus able to achieve a tight bend radii for the bronchoscopic applications described herein.

In embodiments of the invention, a coolant is circulated through the device to compensate for cable heating due to attenuation within the microwave cable.

In embodiments of the invention, the antenna is partially encapsulated by a low microwave energy loss dielectric material limiting the extent to which the coolant can attenuate the microwaves emitted from the antenna. The antenna type may vary. In embodiments, the antenna is selected from the group consisting of a dipole, helical, slot, multiple slot, and monopole-type antenna.

In embodiments, the degree to which the antenna is encapsulated is defined by a ratio of (a) the surface area of the antenna encapsulated to (b) the total surface area of the antenna. In embodiments, the ratio ranges from 0.125 to 1. In other embodiments, the antenna is not encapsulated.

In embodiments of the invention, at least a distal section of the device has a fixed diameter formed from a dual/multi-lumen catheter, thereby having a smaller outer diameter compared to telescoped-tube catheters.

In embodiments of the invention, the temperature along the catheter is controlled by adjusting: dimensions of the catheter lumens to modify coolant flow profiles; coolant temperature; and/or coolant flow rate.

Compared to other ablation energy modalities, the microwave energy applicators in accordance with the present invention have several advantages including: the potential to produce faster heating over larger volumes, less impact from heat sinks, effectiveness in high impedance tissues such as lung, the ability to utilize multiple applicators to produce larger ablation zones, and fewer ancillary components (such as grounding pads). These advantages serve to produce more uniform ablations with shorter treatment times.

These advantages as well as other objects and advantages of the present invention will become apparent from the detailed description to follow, together with the accompanying drawings.

BRIEF DESCRIPTION OF THE DRAWINGS

FIGS. 13A-13B are illustrations of two ablation results in ex vivo porcine loin muscle;

FIGS. 14A-15B are illustrations of various ablation results in porcine lung;

DISCLOSURE OF THE INVENTION

Figure 1:
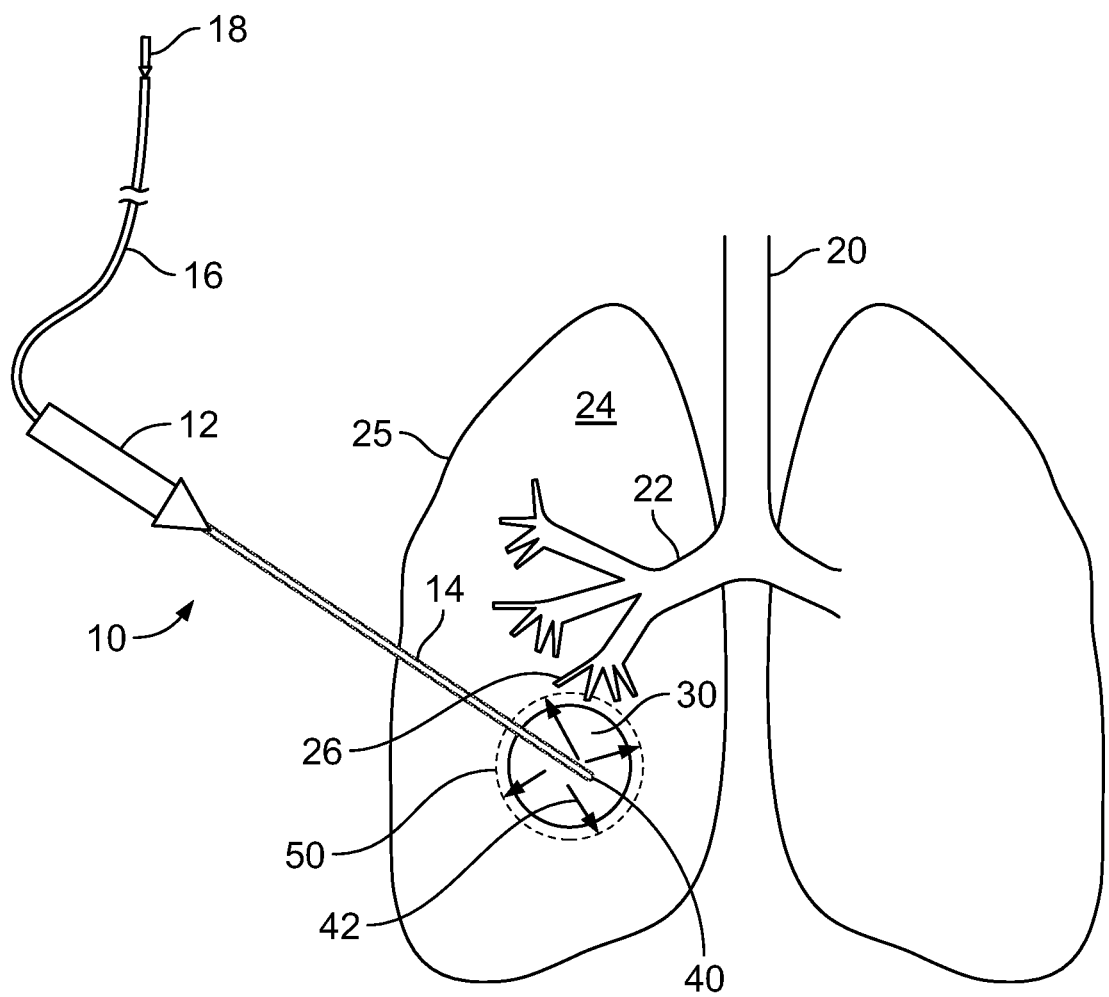
FIG. 1 is an illustration of a percutaneous microwave ablation procedure.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

By the terminology "endoscopic applications" it is meant to include a wide range endoscope-type applications including but not limited to bronchoscopic-type applications. Also by the terminology "applicators", it is meant to include a wide range of energy emitting devices including but not limited to microwave ablation catheters, implements, wands, and rigid probes such as the probes used in a percutaneous approach. It is also to be appreciated that unless defined otherwise, all technical and scientific terms used herein have the same meaning as commonly understood by one of ordinary skill in the art to which this invention belongs.

Described herein are endoscopic-guided microwave ablation devices, systems and methods that enable treatment of central targets, including but not limited to targets that are otherwise inaccessible via a percutaneous approach.

Figure 2:
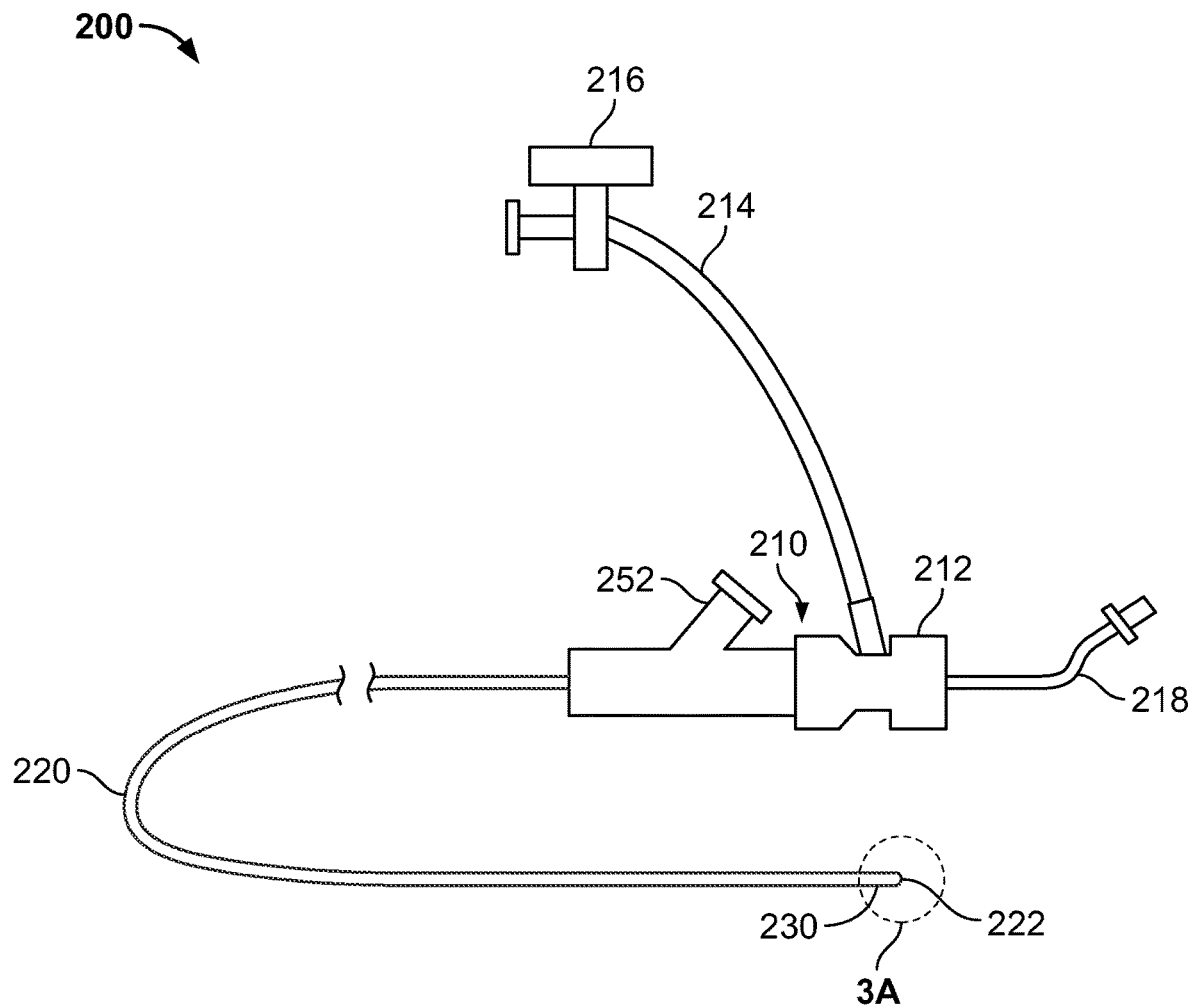
FIG. 2 is an illustration of a microwave ablation catheter in accordance with an embodiment of the invention.

FIG. 2 illustrates a flexible microwave ablation (MWA) catheter 200 having a proximal handle-like section 210 and an elongate tubular shaped body 220, distal section 230, and a distal tip 222.

The length of the catheter may vary. In certain embodiments, the microwave ablation catheter has an insertable length (a length capable of insertion within the patient's body) of at least 0.5 m, at least 0.75 m, at least 1.0 m, or at least 1.25 m. In particular embodiments, the catheter length ranges from about 1 to about 2 m, from about 1.25 m to about 1.75 m, or about 1.5 m.

The proximal section 210 is shown having a first hub 212 and second hub 252 to provide access to the tubular shaft as described further herein. In embodiments, a valve 216 is connected in line with tube 214 to supply a coolant to the catheter 200. An electrical connector 218 is shown extending from the proximal end of the handle. The electrical connector 218 can be coupled to a power supply to provide the microwaves as described further herein. It is also to be understood that the configuration of the proximal section 210 can vary and the invention can incorporate more or less hubs, tubes, valves, and connectors into the handle. In embodiments, the proximal section has a slide-hammer or pistol-like shape to ergonomically accommodate the physician during a bronchoscopic procedure.

Figure 3A:
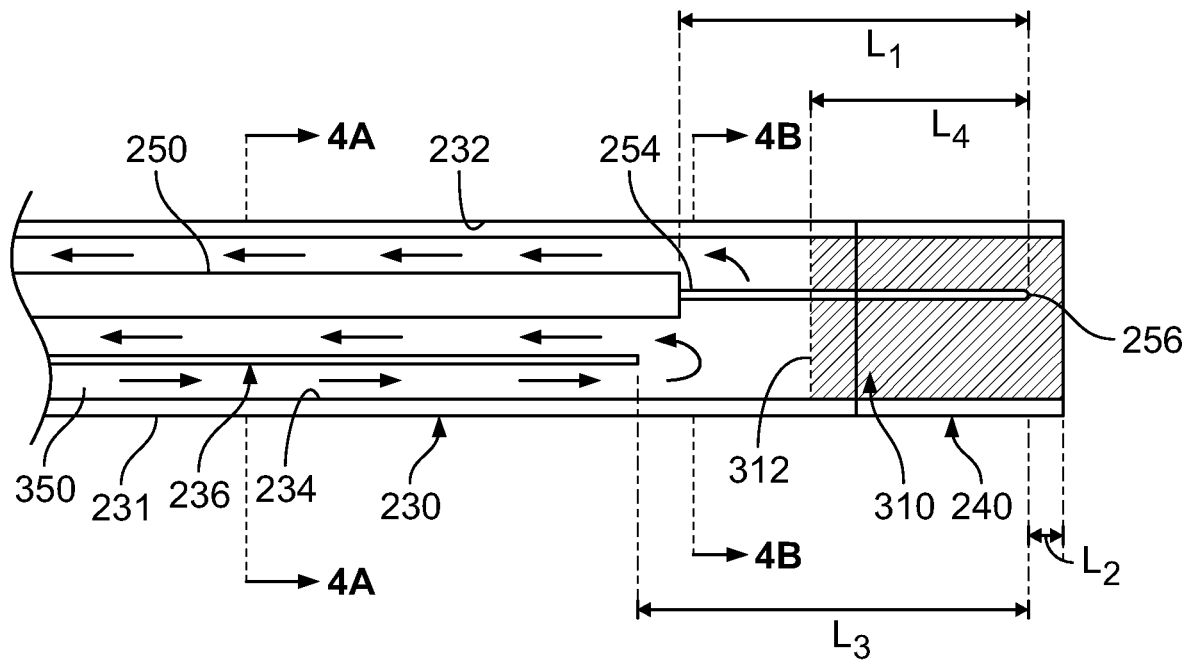
FIG. 3A is an axial sectional view of the distal section of the catheter shown in FIG. 2 according to an embodiment of the invention.

FIG. 3A is an enlarged partial axial section of the distal section 230 of the catheter 200 shown in FIG. 2 according to an embodiment of the invention. The catheter 200 is shown including a generally tubular body formed by a multi-lumen section 231 coupled to a single lumen segment 240. An antenna 254 is shown extending a distance $L_1$ from a transmission line 250, both of which are disposed within the single lumen segment 240 of the distal section of the catheter. The tubular body is shown extending a distance $L_2$ from the end of the antenna. The distances $L_1$ and $L_2$ can be selected based on the electromagnetic wavelength, and may vary. It is noted that the electromagnetic wavelength is a function of the system operating frequency, and the electrical properties of the materials surrounding the antenna, including the coolant, dielectric encapsulating plug, catheter, and/or lung tissue. For a system operating at a frequency of about 2.45 GHZ, for example, the distance $L_1$ ranges from 4-24 mm and the distance $L_2$ ranges from 0.5-3 mm.

The multi-lumen section 231 is a dual lumen or side by side lumen catheter having a wall 236 for separating the lumens. Wall extends the length of the catheter and is shown terminating a distance $L_3$ from the tip of the antenna 256. In embodiments, the distance $L_3$ ranges from 7-28 mm.

The two lumens shown in FIG. 3A include a liquid outflow passageway 232 and a liquid inflow passageway 234 that can extend the length of the catheter body. A coolant 350 is circulated through the liquid outflow passageway 232 and liquid inflow passageway 234 serving to cool the catheter body and reduce collateral damage to tissue during ablation. An example of a coolant is water. Although lumens 232 and 234 are identified as outflow and inflow lumens respectively, the direction of the circulating liquid may be reversed. In embodiments, the coolant 350 is driven towards the target tissue through lumen 232 and away from the target tissue through lumen 234.

FIG. 3A also shows a portion of antenna 254 encapsulated by an insulator 310. The insulator is preferably a low-loss dielectric material. Non-limiting examples of low-loss dielectric materials suitable for insulator include PTFE (Teflon), FEP, ceramics (e.g. Alumina) and epoxies. Microwaves can pass through the insulator, but not electrical current. Additionally, as discussed herein, the insulator desirably modifies the shape of the radiation pattern by limiting the extent to which the coolant may travel in relation to the antenna. In embodiments, the insulator is set a threshold distance $L_4$ from the antenna distal tip such that the coolant attenuates only a portion of the microwave energy during ablation.

Without intending to being bound to theory, the rationale for partial or incomplete-encapsulation of the antenna is that in some embodiments, e.g. monopole type antennas as shown in FIG. 3A, the antenna radiation pattern is relatively long. That is, the radiation pattern extends proximally along the cable resulting in a longer than desired ablation zone. To restrict the length of the ablation zone, water is circulated around the proximal part of the monopole, but the distal tip remains encapsulated in epoxy 310 (or other low-loss dielectric material). Thus, microwaves traveling proximally are attenuated by the water.

Although there is also some attenuation of the microwaves traveling radially outward from the antenna and into the tissue, we have found that the described designs are sufficient for lung applications described herein where a desired ablation zone size ranges from 1-10 cm, more preferably from about 2-5 cm, and in some embodiments, about 3-4 cm in diameter.

With reference again to FIG. 3A, a liquid barrier 312 is shown at a predetermined distance $L_4$ from the antenna distal end 256. The distance $L_4$ may vary. In embodiments, the distance $L_4$ ranges from 2-12 mm. Additionally, in embodiments the distance $L_4$ is a fraction of the length $L_1$ and may range from $\frac{1}{8} \times L_1$ to $1 \times L_1$.

Thus, in embodiments, the liquid is transported substantially close or into contact with the antenna thereby absorbing the microwave energy corresponding to the radiating pattern tail while permitting the microwave energy to pass to the target tissue. As mentioned above, the liquid barrier 312 may be formed variously. In embodiments, the liquid barrier is formed using epoxy 310, which also serves to bond the antenna, multi-lumen tube 231, and single lumen tubular element 240 together.

Although the catheter tubular body is shown as a combination of tubular segments, the catheter configuration may vary widely. The tubular catheter or body may have more or less segments and lumens. The catheter body may enclose or house a plurality of individual tubes or tube bundles and/or incorporate telescoping-type arrangements. The catheter lumens and segments may be integral with or separately coupled to serve the applicators described herein.

Figure 4A:
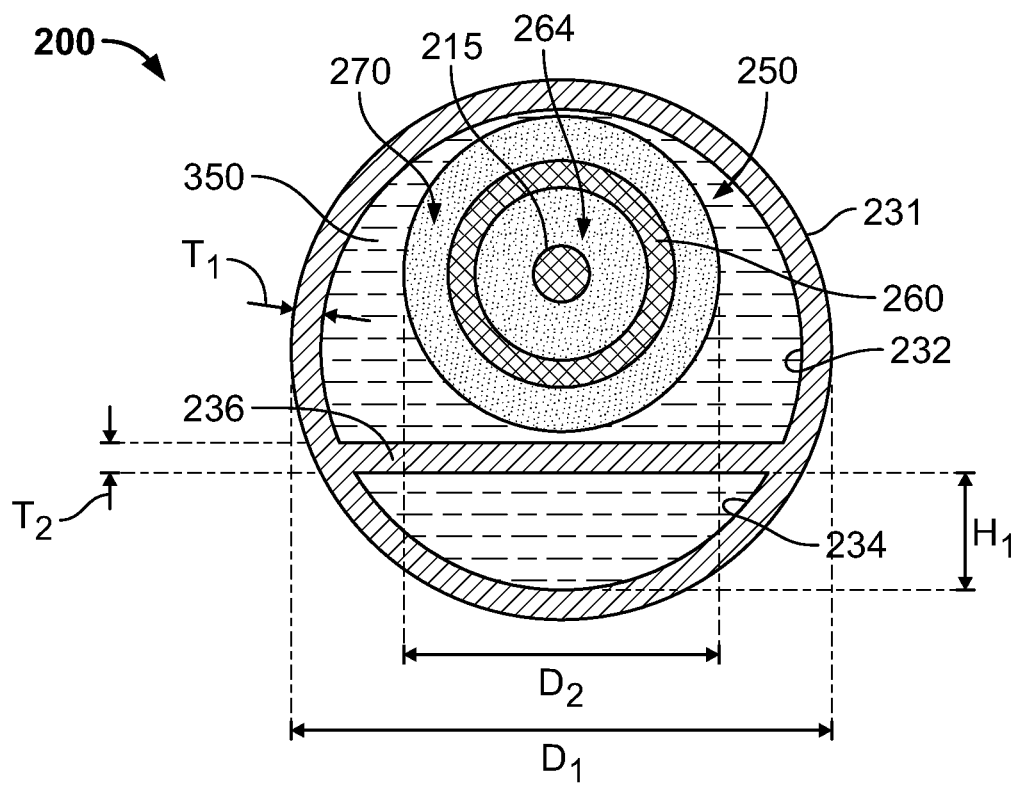
FIG. 4A is a cross sectional view of the catheter shown in FIG. 3A taken along line 4A-4A.

FIG. 4A is an enlarged cross sectional view taken along line 4A-4A of the catheter 200 shown in FIG. 3A. Tubular outer member of the distal section 230 is shown surrounding transmission line 250. In embodiments, the tubular body has a wall thickness $T_1$ ranging from 0.001 to 0.005 in. The diameter of tubular outer member preferably is less than 2 mm so as to be advanceable through the working lumen of a bronchoscope or endoscope. In embodiments, the outer diameter $D_1$ of the tubular member 230 is less than 5 mm, less than 3 mm, or less than 2 mm in order to fit within the working channels of available scopes.

The outer tubular body 231 in FIG. 4A is divided into a liquid inflow lumen 234 and liquid outflow lumen 232 by wall 236. In embodiments, wall 236 has a thickness $T_2$ ranging from 0.001 to 0.005 in. The wall is spaced at a height $H_1$ from the bottom of the tubular body 230 ranging from 0.01 to 0.02 in. Each of the liquid outflow lumen 232 and liquid inflow lumen 234 are shown filled with liquid 350.

As stated herein, the liquid serves both as a coolant and microwave energy absorber. An exemplary liquid is water. The extent that the microwave antenna radiating element is surrounded by water can be adjusted to control the amount of microwave energy traveling backwards and heating non-targeted objects (e.g., airways, scope, blood vessels, the heart). Use of materials other than water (e.g., materials with different dielectric properties) provides another means for adjusting backwards radiation. Selection of the optimal material(s) and length of radiating element in contact with the material(s) provides a means for limiting backward radiation without increasing device diameter. In embodiments, and as discussed further herein, the coolant attenuates a tail end of the radiation pattern.

The transmission line 250 shown in FIG. 4A includes an inner conductor 215 and outer conductor 260 separated by a dielectric layer 264. The transmission line 250 also has an outer sheath or jacket 270 which may be an electrically non-conducting material such as for example a plastic. In embodiments, the diameter $D_2$ of the transmission line ranges from 1 to 1.3 mm. The transmission line extends through the body of the catheter from the proximal section to the distal section and serves to transmit a microwave signal or energy from the power supply to the antenna, as described further herein.

In embodiments, the transmission line is constructed of a thin and flexible coaxial cable, with bend radius suitable for reaching ablation targets via a bronchoscopic/endoscopic approach. In embodiments, the bend radius is on the order of 2.5 cm, 2.0 cm, 1.5, cm, 1 cm, or less. In embodiments, the outer conductor 260 is a braided electrically conducting material or filament structure for improved flexibility along the length of catheter. In embodiments, the inner conductor 254 is also a braided electrically conducting material.

The use of coaxial cables with braided center and outer conductors as described herein considerably enhances flexibility. In addition, the use of a coaxial cable with outer plastic jacket reduces "set", a phenomena where the instrument exiting the working channel of the endoscope takes a path other than the path defined by the endoscope's tip, and improves cooling efficiency. Amongst other things, the plastic jacket adds a layer of thermal insulation and provides a low friction flow surface.

Figure 4B:
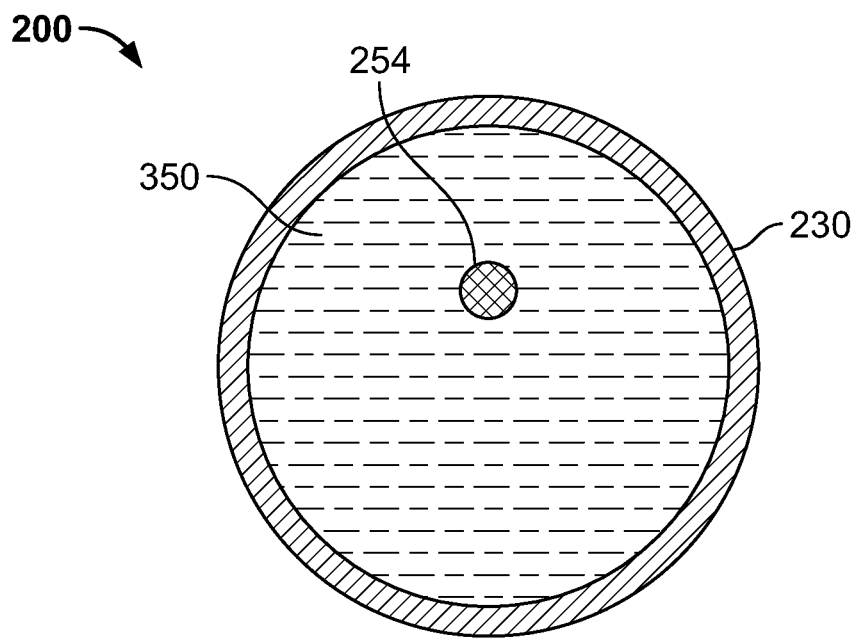
FIG. 4B is a cross sectional view of the catheter shown in FIG. 3A taken along line 4B-4B.

FIG. 4B is an enlarged cross sectional view taken along line 4B-4B of the catheter 200 shown in FIG. 3A. Tubular outer member 240 is shown surrounding antenna 254. An annular space is shown filled with liquid 350. The liquid makes direct contact with the antenna, cooling the antenna as well as absorbing energy during activation of the microwave energy. As described herein, the shape and pattern of the radiating energy is adjusted by setting the liquid barrier 312 closer or farther from the tip of the antenna.

Figure 5:
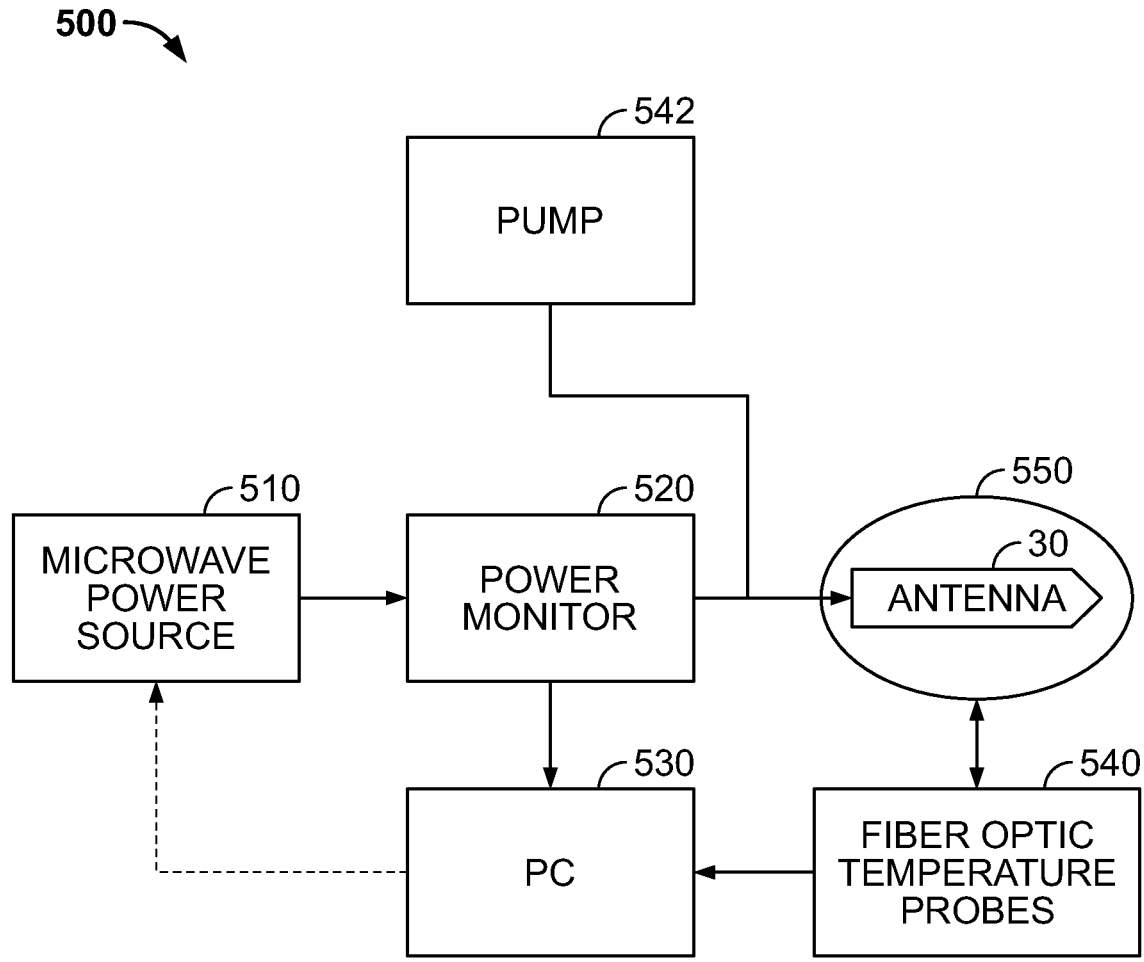
FIG. 5 is a schematic diagram of a microwave ablation system in accordance with an embodiment of the invention.

FIG. 5 schematically depicts an exemplary electrosurgical system 500 constructed in accordance with one embodiment of the present invention. An electromagnetic power source 510 generates and transmits the desired microwave energy to antenna 30. Electromagnetic power source 510 may include a microwave signal generator, a DC power supply, a power amplifier (not shown). Power monitor 520 monitor's electrical activity to and from the device 30 such as, for example, reflected power impedance. The operation of device 30 and the various components of equipment utilized by power source 510 may be monitored and controlled by a microprocessor, such as in a personal computer 530, server, or a handheld device.

FIG. 5 also shows a pump 542 in fluid communication with the MWA applicator. The pump serves to circulate the liquid through the MWA applicator. Adjusting the flowrate can be used to affect the catheter temperature and radiation pattern described further herein. Exemplary flowrates range from 5-40 ml/min. An example of a pump is a peristaltic pump. However, other means as is known to those of skill in the art may be used to drive the liquid through the MWA applicator including electric pumps, syringes, gravity drip feeds, etc.

In embodiments, the frequencies generated by the signal generator are similar to those that are associated with the frequencies typically used to heat water. In embodiments, the frequencies generated range from about 800 MHz to 6 GHz, from about 900 MHz to about 5 GHz, or from about 1 GHz to about 3 GHz. In preferred embodiments, particularly for devices used for experimental clinical work, the frequencies generated are 915 MHz or 2.45 GHz. Operating at an operating frequency of 2.45 GHz is desirable because the higher frequency option results in smaller antenna physical dimensions due to a shorter wavelength. This is helpful in miniaturizing the length of the active portion of the device. In some embodiments, the MWA system is operated from about 5-6 GHz. Furthermore, MWA systems operating at 2.45 GHz produce more spherical/symmetric ablation zones than 915 MHz, which is helpful in minimizing the volume of ablated healthy tissue when targeting small malignancies.

FIG. 5 also shows temperature probes 540. Temperature probes 540 can optionally be inserted into the tissue 550 along with device 30 so as to monitor the temperature of tissue being ablated and adjacent to the tissue being ablated. In embodiments, fiber optic (or other non-metallic) temperature sensors are employed. Or, temperature sensors may be incorporated into the devices by use of thermistors or thermocouples placed on an exterior of the shaft of the device or within the liquid near the distal tip so as to monitor temperature, and/or changes in temperature during an ablation.

As described herein, in embodiments, antenna 30 is designed to have an impedance close to that of the transmission line from signal generator (nominally, 50 ohms) at the operating frequency. The impedance presented by antenna 30 is a function of the dimensions of the antenna as well as the wavelength at the operating frequency. Because of this impedance matching, the device can be used in methods of treating body tissues that are in close proximity to critical structures. See also US Patent Publication No. 2017/0265940 to Prakash et al, herein incorporated by reference in its entirety.

Figure 6A:
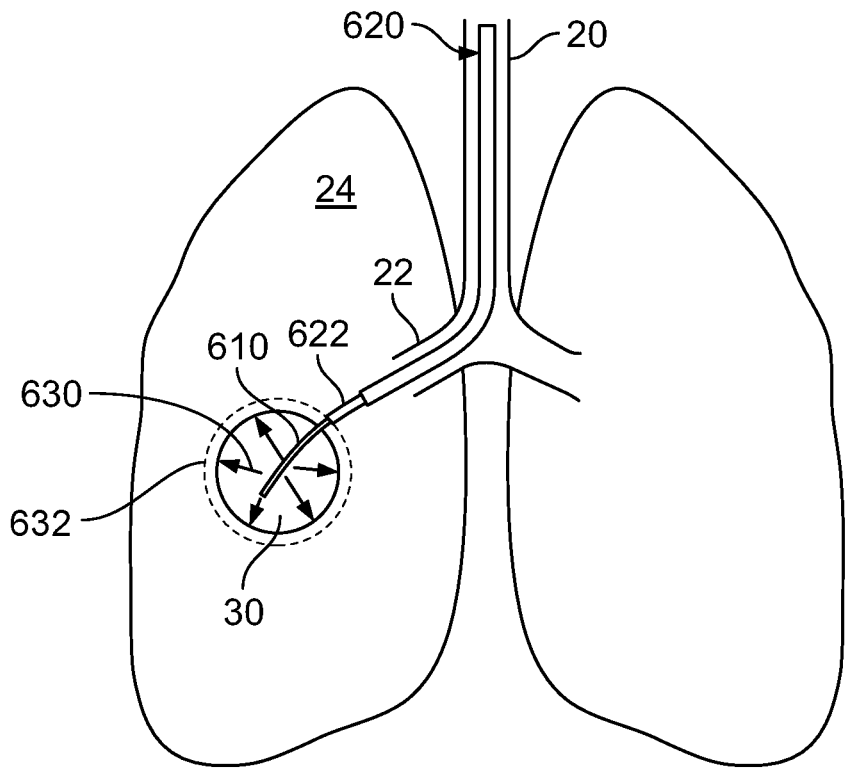
FIGS. 6A-6B are illustrations of bronchoscopic microwave ablation procedures corresponding to emitting radiation in different directions.

FIG. 6A is an illustration of a bronchoscopic microwave ablation procedure on a tumor 30 in the lung 24 of a patient. Initially, a bronchoscope 620 is advanced through the nose or mouth into the trachea 20 and mainstem bronchi 22. A guidance sheath 622 is shown advanced through the scope, and towards the target tissue 30. The MWA catheter 610 is then advanced from the guidance sheath 622 or bronchoscope 620 into the tumor 30.

As described herein, in embodiments, the MWA catheter has a pre-set shape which facilitates the tip of the catheter 610 to push through parenchymal tissue in the lung 24. The catheter may include tubular layer or spine elements formed of materials that provide pushability such as Nitinol or other superelastic materials.

With reference to FIG. 6A, the catheter 610 is shown advanced substantially along a central axis of the tumor 30. The emitted microwave radiation 630 is omnidirectional. The radiation is emitted in all directions from the distal section of the catheter 610. It is desirable to achieve such spherical ablation zones 632 because such predictable zones aid practitioners in planning applicator position relative to the target. In preferred embodiments, the bronchoscopic MWA applicator 610 is capable of treating tumors up to 20 mm in diameter (perhaps ~30 mm ablation zones).

It is also desirable to circulate coolant to mitigate the heat created during the ablation and to reduce collateral damage to the non-target tissues (e.g., the trachea 20, bronchi 22, blood vessels, and the heart) and to the instrumentation (e.g., the scope 22).

Additionally, as described herein, the coolant flowpath is determined to circulate coolant along the body of the catheter for cooling purposes, and also to absorb a desired amount of radiation emitted from the antenna, thereby defining or limiting the radiation pattern arising from the antenna. Embodiments of the invention include providing a liquid barrier at a predetermined distance from the antenna tip to allow the coolant to flow across the antenna or in close proximity to the antenna thereby absorbing a desired amount of radiation.

Figure 6B:
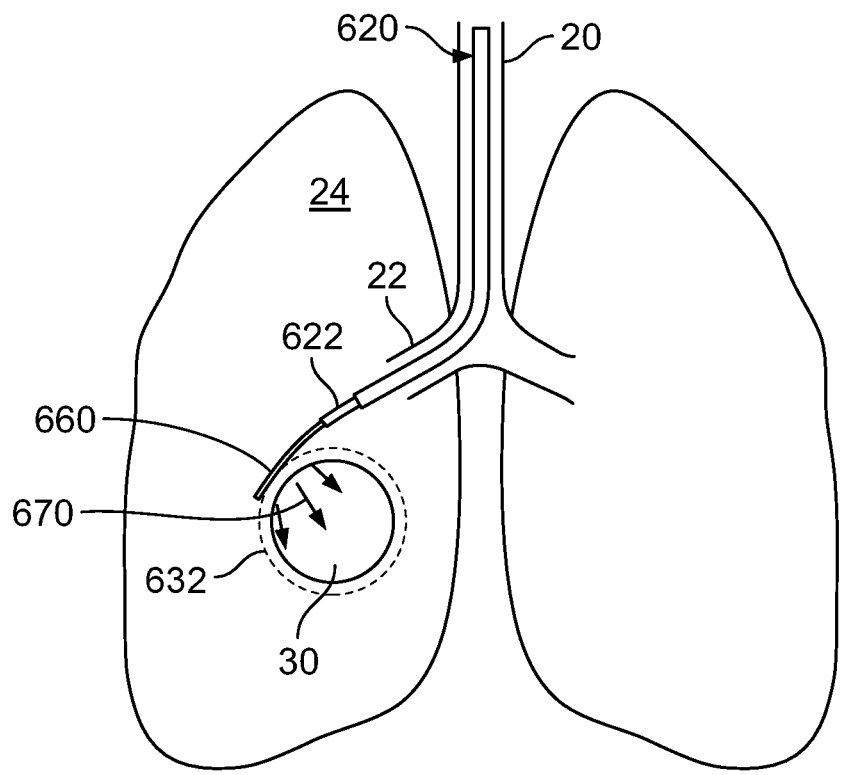

FIG. 6B is another illustration of a bronchoscopic microwave ablation procedure on a tumor 30 in the lung 24 of a patient. The procedure shown in FIG. 6B is similar to that shown in FIG. 6A except the MWA catheter 660 is configured to emit microwave energy directionally 670.

The MWA catheter 660 is configured to emit microwave energy only toward the targeted tissue 30 with a directional radiation pattern 670. The physician or operator of the device may orient the device such that energy is emitted substantially toward the target structure and away from the critical tissues that should not be damaged. Examples of devices adapted to emit the microwave energy directionally are described in US Patent Publication No. 2017/0265940 to Prakash et al, herein incorporated by reference in its entirety.

Figure 7:
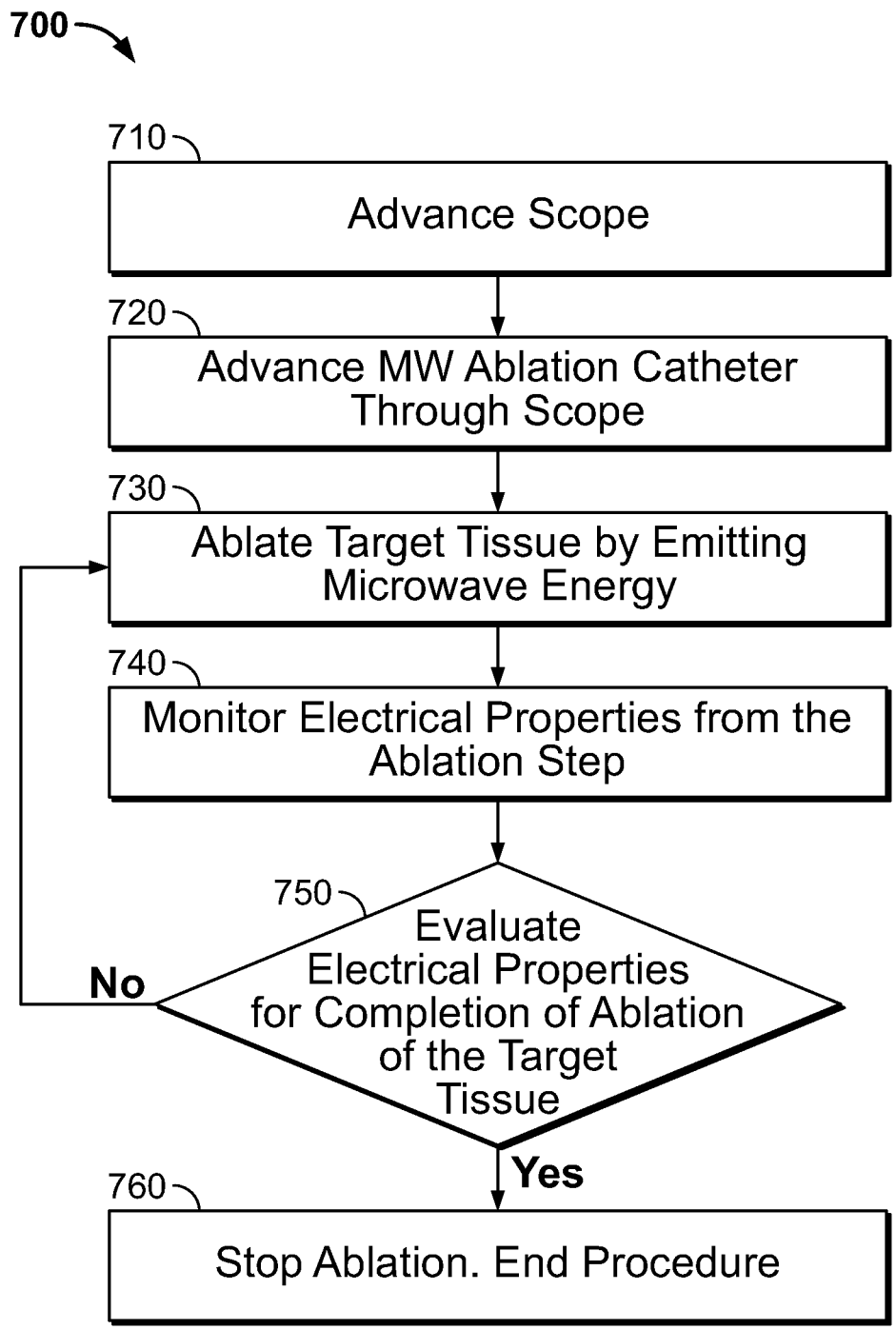
FIG. 7 is a flow diagram of a method for microwave ablation of a target tissue.

FIG. 7. Shows a flow chart of a microwave ablation method 700 in accordance with an embodiment of the invention.

Step 710 states to advance the scope. In embodiments, a bronchoscope is advanced into the patient's lung via the mouth or nasal passageways. Examples of scopes include without limitation a bronchoscope, endoscope, colonoscope, etc.

Step 720 states to advance the microwave ablation catheter through the scope. The physician advances the MWA catheter through the working lumen of the scope, or through an optionally placed guidance sheath which has been advanced through the scope, and towards the target. Examples of targets include without limitation tumors and suspect tissue growths. In embodiments, the microwave ablation catheter is advanced through a central axis of the tumor.

Step 730 states to ablate target tissue by emitting microwave energy. As described herein, microwave power is transmitted to the end of the antenna and emitted therefrom. The radiation pattern can vary. In embodiments the radiation pattern is cylindrically symmetric about the axis of the antenna.

Additionally, the radiation pattern may be adjusted by circulating coolant in the vicinity of the antenna. In embodiments, the radiation pattern is modified by defining a liquid barrier a predefined distance from the end of the antenna. Preferably, the radiation pattern is limited or confined to the ablation zone near the distal section of the catheter. The proximal region of the radiation (namely, the tail) is limited by the presence of the circulating coolant.

Step 740 states to circulate coolant as described herein.

Step 750 states to evaluate whether a threshold limit has been reached (e.g., time, or temperature). If the threshold limit is not reached, the ablation is continued as indicated by returning to step 730. In embodiments, the ablation time or treatment time may be continuous, and range from 1-15 minutes, more preferably between 2-5 minutes, frequency ranges between at 915 MHz or 2.45 GHz, and more preferably between 2.0 and 2.5 GHz.

In addition to continuing the ablation, the measurements discussed herein may be used to guide the adjustment of applied power during the procedure. The power may be adjusted higher or lower or otherwise adjusted based on feedback from the measurements. The processor can be programmed to determine when and how to adjust the power based on the measured properties.

Finally, step 760 states to stop ablation. The procedure is complete.

EXAMPLES

A prototype device was fabricated and evaluated via computer model simulation. Ex vivo porcine tissues were ablated to verify simulation results and serve as proof-of-concept. Additional in vivo experiments were conducted in healthy porcine and canine lung tissue.

To assess technical feasibility of delivering MWA via a bronchoscopic approach, we constructed and tested a water-cooled, coaxial monopole antenna. The antenna was constructed by stripping away the outer shield of the coaxial transmission cable and exposing the center conductor. An antenna length of 14 mm was calculated based on the expected wavelength of the radiated electromagnetic wave in lung tissue. Although coaxial antennas without a balun/choke are known to yield radiation patterns with a significant tail, the limited space within 2 mm diameter applicators precluded the use of a balun.

Example 1

Computer Model Simulation

Coupled finite element method (FEM) electromagnetic—heat transfer simulations were used to characterize antenna design specific to lung tissue. The FEM simulations were employed to assess the antennas impedance matching, radiation pattern, and thermal ablation profile.

Simulations employed tissue properties as detailed in J. Sebek, N. Albin, R. Bortel, B. Natarajan, and P. Prakash, "Sensitivity of microwave ablation models to tissue biophysical properties: A first step toward probabilistic modeling and treatment planning," Med. Phys., vol. 43, no. 5, p. 2649, May 2016.

Figure 8:
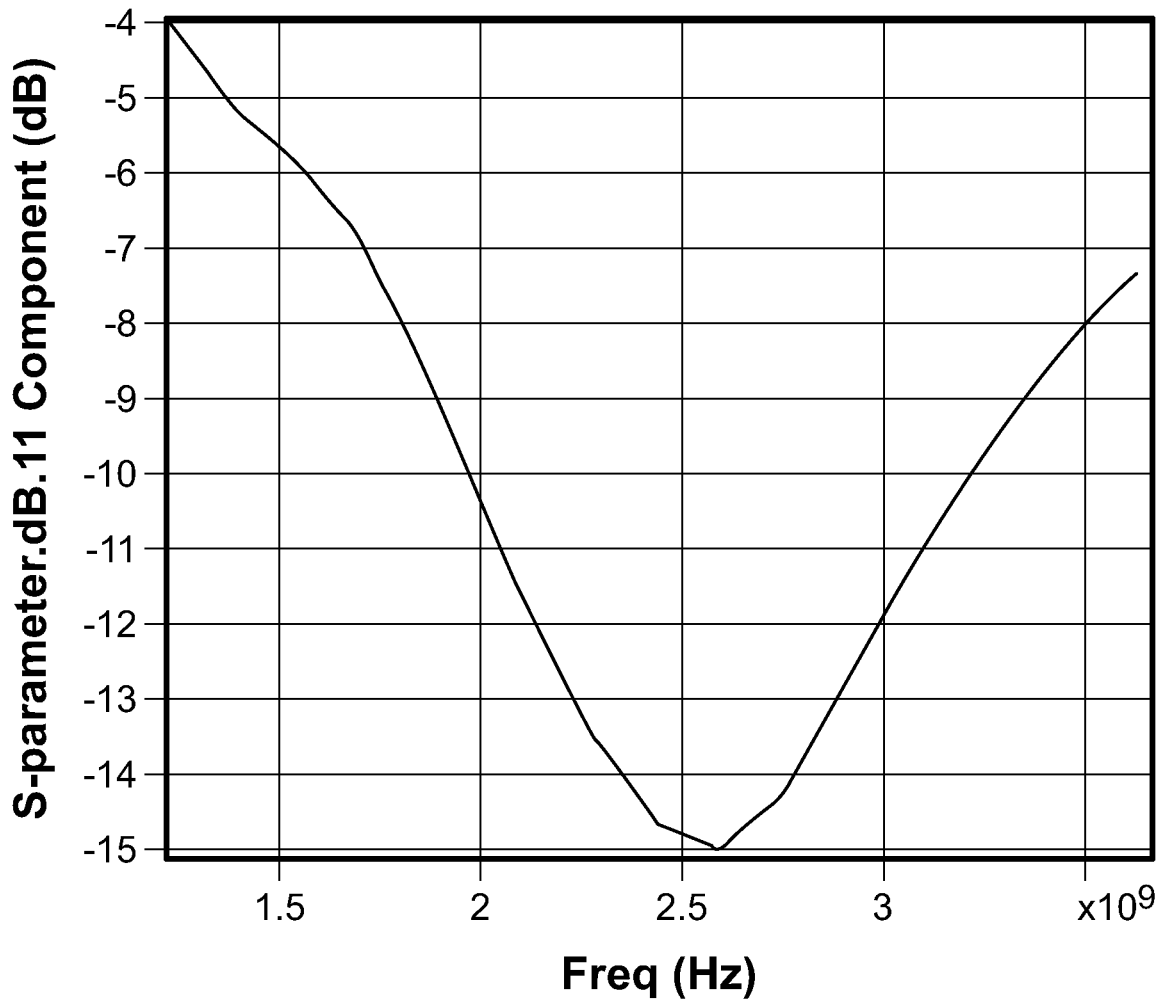
FIG. 8 is a graphical representation of the simulated antenna reflection coefficient for a MWA applicator in lung tissue.

FIG. 8 illustrates the simulated antenna reflection (SAR) coefficient, $S_{11}$. The $S_{11}$ parameter is a measure of the impedance match between the coaxial transmission line and the antenna. Smaller (i.e. more negative) $S_{11}$ values indicate a good impedance match between the transmission line and the antenna. Power radiated by the antenna is absorbed within surrounding tissue. Conversely, larger $S_{11}$ values indicate increased reflected power, which would result in reduced power delivered to tissue, and increased heating within the coaxial feedline. FIG. 8 indicates the evaluated MWA catheter has an optimal SAR (namely, lowest) at a frequency of about 2.5 GHz.

Figure 9:
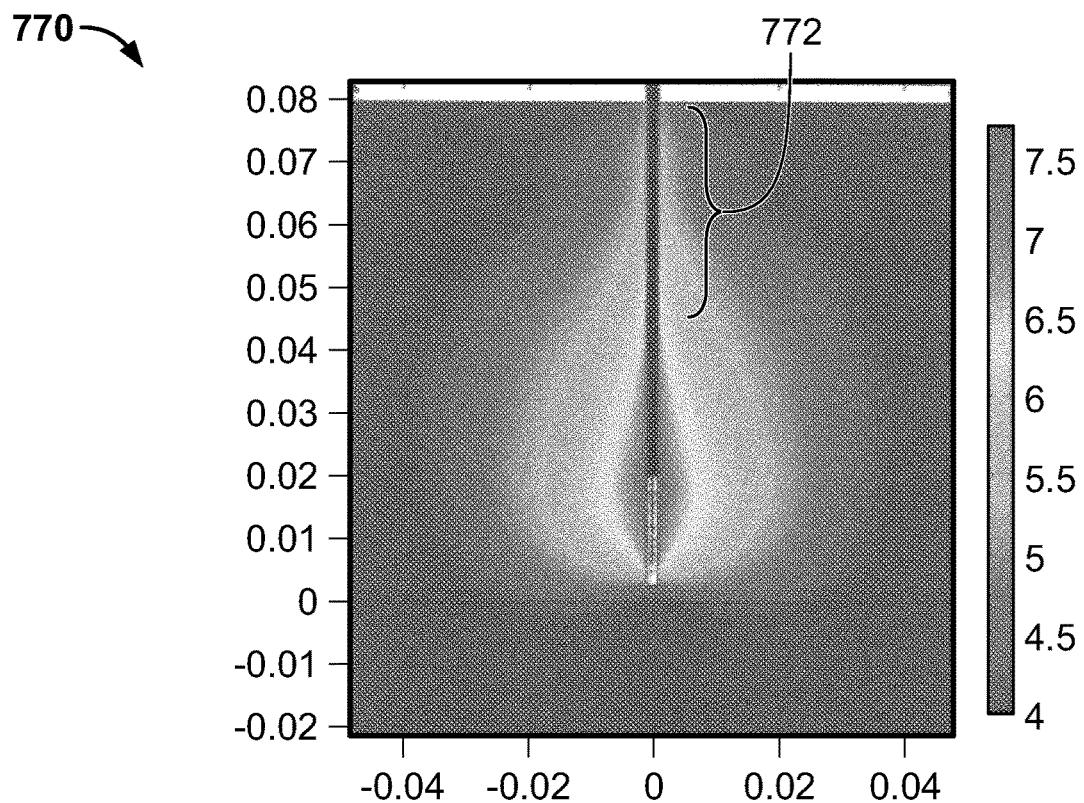
FIG. 9 is a graphical representation of the simulated SAR profile of a flexible MWA applicator.

FIG. 9 illustrates a simulated SAR profile 770 of the MWA applicator described above. As shown, the profile has a proximal tail 772 which tapers to the shaft with distance from the distal tip.

Figure 10:
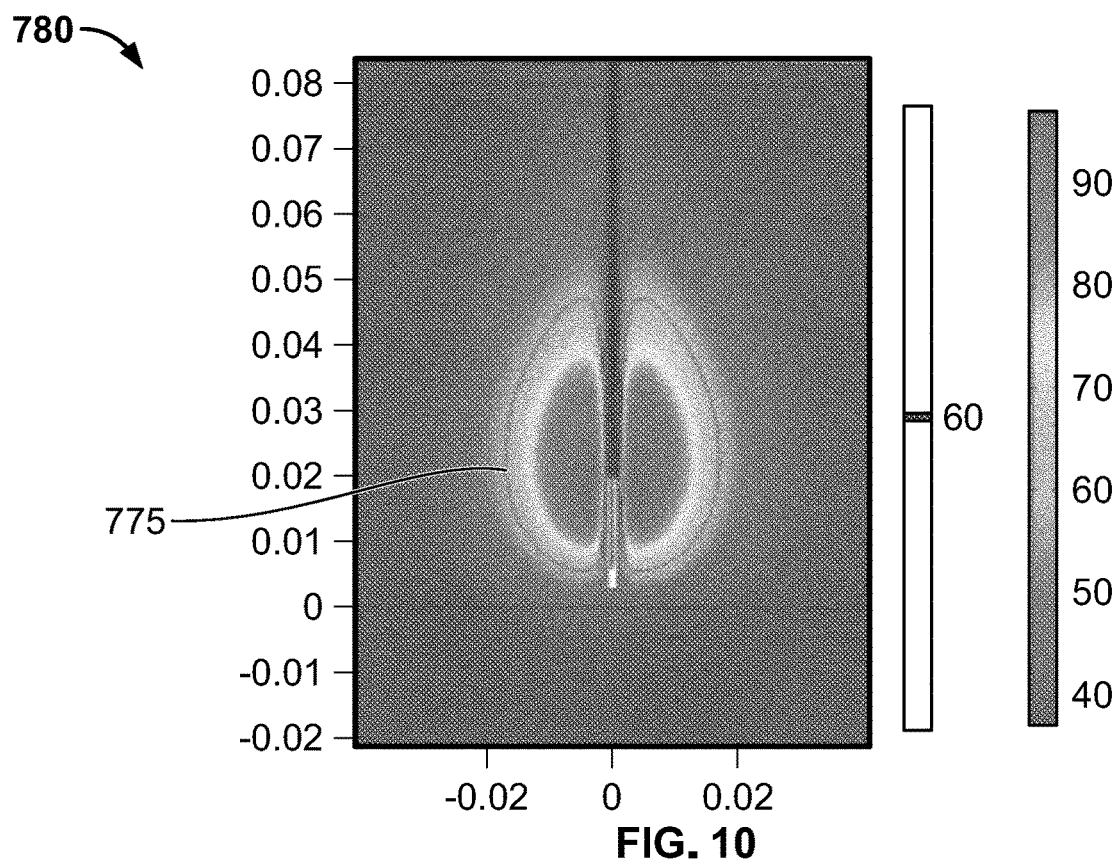
FIG. 10 is a graphical representation of the simulated ablation zone temperature profile.

FIG. 10 illustrates a simulated transient temperature profile 780. Electromagnetic simulations were coupled with a heat transfer model to simulate the transient temperature profile following ablation with 40 W applied power for 300 s. The 60° C. isothermal contour line 775, as an estimate of the anticipated ablation is overlaid on the simulated temperature profile. This indicates the evaluated MWA catheter causes a spherical ablation zone.

Example 2

Ex Vivo Porcine Muscle

Figure 11:
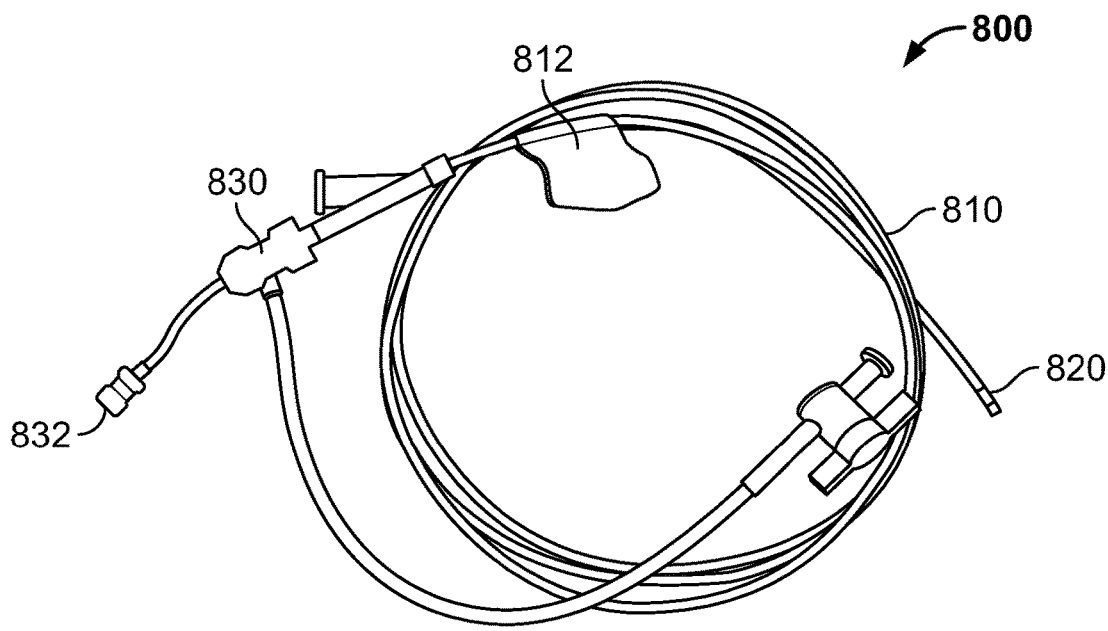
FIG. 11 is an illustration of a prototype MWA applicator.

With reference to FIG. 11, a prototype flexible applicator 800 was fabricated using a 1.3 m long coaxial microwave transmission cable jacketed by custom extruded multi-lumen tubing 810 as described above. We used Vestamid tubing. The tubing 810 provides the flow path for cooling water and a low friction protective outer surface. The applicator 800 is less than 2 mm in total outside diameter. The distal end of the device is sealed with an epoxy plug.

A hemostasis valve 830 at the proximal end of the device allows insertion of the coaxial cable 832 into the extruded tubing and provides connection for the circulating water system. Ice water was circulated with a peristaltic pump (not shown). The cooling system removes heat coming from cable attenuation and reflected power to prevent device damage and unintended heating of surrounding healthy tissue.

Figure 12A:
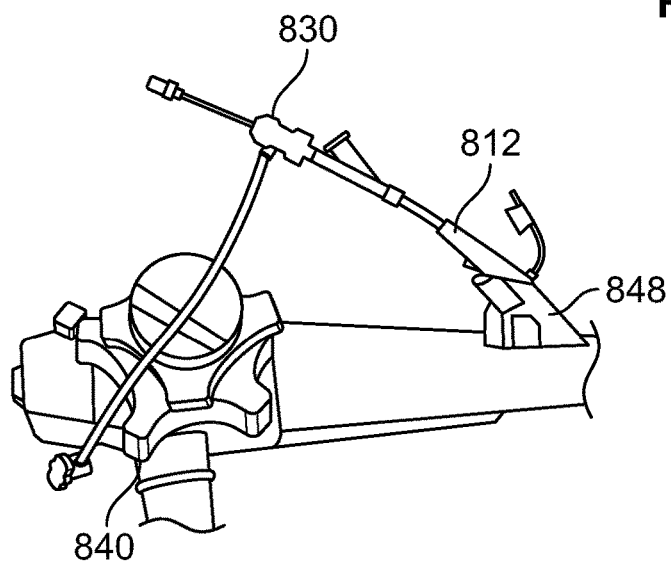
FIG. 12A is a partial illustration of the prototype MWA shown in FIG. 11 inserted into the proximal end of a working channel of a bronchoscope.

FIG. 12A is an enlarged partial view of the proximal section of a bronchoscope 840 and illustrates the flexible MWA applicator 800 shown in FIG. 11 inserted into a hub 848 of a bronchoscope. The MWA applicator is advanced to marker 812, corresponding to a predetermined distance the applicator tip 820 shall be extended from the bronchoscope end 842.

Figure 12B:
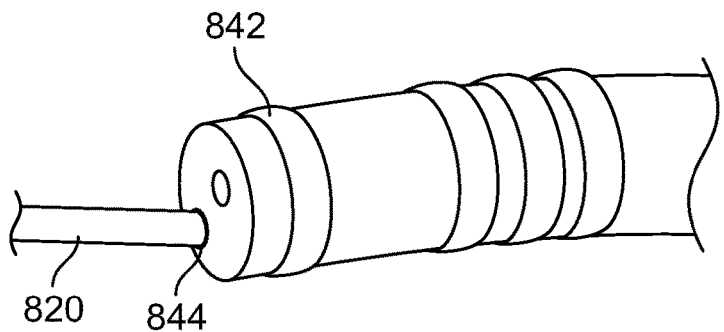
FIG. 12B is a partial illustration of the prototype MWA shown in FIG. 11 extending from the distal end of the working channel of the bronchoscope.

FIG. 12B is an enlarged partial view of the distal section 842 of the bronchoscope and illustrates the distal section of the flexible MWA applicator 800 shown in FIG. 11 extending distally from the working lumen 844 of the bronchoscope.

Both porcine loin muscle and lung tissues were obtained fresh and kept in sealed bags placed on ice for use in device characterization. Prior to use, the tissue was sectioned into approximately 10 $cm^3$ samples and warmed to approximately 30° C. in a water bath (while sealed in plastic bags). The MWA applicator and four fiber optic temperature sensors were inserted 6 cm into the tissue using a plexi-glass template which kept the sensors spaced 5, 10, 15, and 20 mm radially from the applicator.

A HP 8665B signal generator and RFcore RCA0527H49A microwave amplifier were used to supply the 2.45 GHz signal to the applicator. Forward and reflected power were monitored during the experiments using a Bird Technologies 7022 statistical power meter.

Ablation zones created with the flexible MWA applicator were first evaluated within the ex vivo pork loin muscle tissue. Three ablations were performed and the results are summarized in Table 1 below. FIGS. 13A-13B show representative ablation zones when the tissue is sectioned along the axis of the tissue.

TABLE 1

Ablation results in porcine muscle

| Power (W) | Duration (min) | Height (mm) | Diameter (mm) | Axial Ratio |
|---|---|---|---|---|
| 40 | 4 | 27 | 19 | 0.70 |
| 40 | 4 | 33 | 24 | 0.73 |
| 40 | 4 | 27 | 17 | 0.63 |
| Mean | | 29 | 20 | 0.69 |
| Std. dev. | | 3.5 | 3.6 | 0.05 |

Example 3

Ex Vivo Porcine Lung

Next, with the applicator inserted into lung tissue, an appropriate impedance match was confirmed when the antenna $S_{11}$ of −21.8 dB was measured at 2.45 GHz using an HP 8753D vector network analyzer. Examples of desirable impedance matches range from −8 to −25 dB.

The first ex vivo lung ablation performed at 40 W as measured by the power meter did not produce any visible ablation region. This may have been due to applicator positioning within a large airway, described further herein. Results from additional ablations performed at 60 and 80 W are given in Table 2 below.

TABLE 2

Ablation results in porcine lung

| Power (W) | Duration (min) | Height (mm) | Diameter (mm) | Axial Ratio |
|---|---|---|---|---|
| 40 | 4 | — | — | — |
| 60 | 5 | 31 | 13 | 0.42 |
| 60 | 5 | 32 | 10 | 0.31 |
| 60 | 5 | — | — | — |
| 80 | 5 | 32 | 13 | 0.41 |
| 80 | 5 | 17 | 15 | 0.88 |

FIGS. 14A-14B show results for the two 60 W, 5 min, porcine lung ablations.

FIGS. 15A-15B show results for the two 80 W, 5 min, porcine lung ablations.

We also noted the third ablation performed at 60 W exhibited a barely visible ablation zone; its boundary was so faint and diffuse that it could not be accurately measured. The experimentally observed ex vivo ablation zones were anticipated to be smaller than simulated ablation zones because effects such as power lost to cable attenuation and tissue contraction, amongst other things, were not modeled. C. L. Brace, T. A. Diaz, J. L. Hinshaw, and F. T. Lee, "Tissue contraction caused by radiofrequency and microwave ablation: a laboratory study in liver and lung," J. Vasc. Interv. Radiol. JVIR, vol. 21, no. 8, pp. 1280-1286, August 2010.

Collectively, the data and FIGS. 13A, and 13B show the ablation patterns observed in porcine muscle were in close agreement with simulations (diameter=20 mm, height=29 mm, axial ratio=0.69 in experiments vs. diameter 32 mm, height 42 mm, axial ratio=0.76 from simulation). However, ablation zones observed in lung tissue were variable and not in complete agreement with the simulated ablation zone shapes/sizes. Without being bound to theory, the variability in the lung tissue arises due to its spongy nature. Lung tissue is more heterogeneous than muscle due to the number of large diameter airways. These airways cause significant electromagnetic reflection which can affect the consistency of results and the visible appearance of experimental ablation zone. Lung is also much more elastic than other tissues which can cause sample tissue deformation or inaccurate applicator/probe placement during experiments. Further characterizing and predicting ablation size and shape in ex vivo lung tissue, including a suitable tumor mimic, is the subject of ongoing work. T. Kawai et al., "Creation of a tumor-mimic model using a muscle paste for radiofrequency ablation of the lung," Cardiovasc. Intervent. Radiol., vol. 32, no. 2, pp. 296-302, March 2009.

Figure 16:
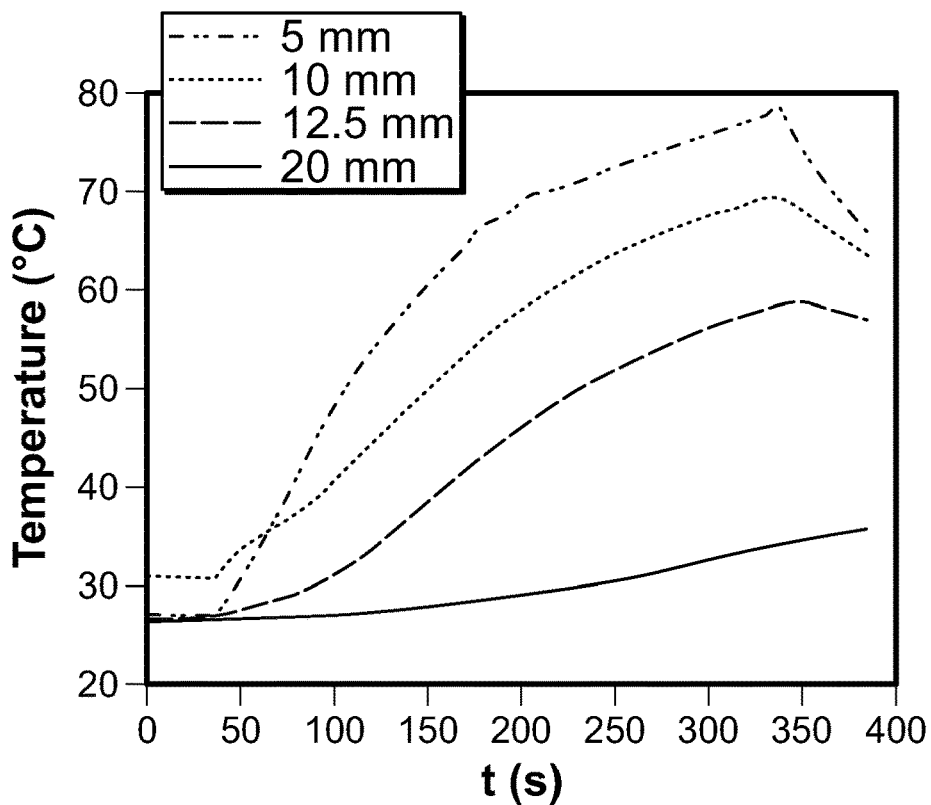
FIGS. 16-17 are a graphical representation of radial temperature vs. time during a lung ablation at various powers.
Figure 17:
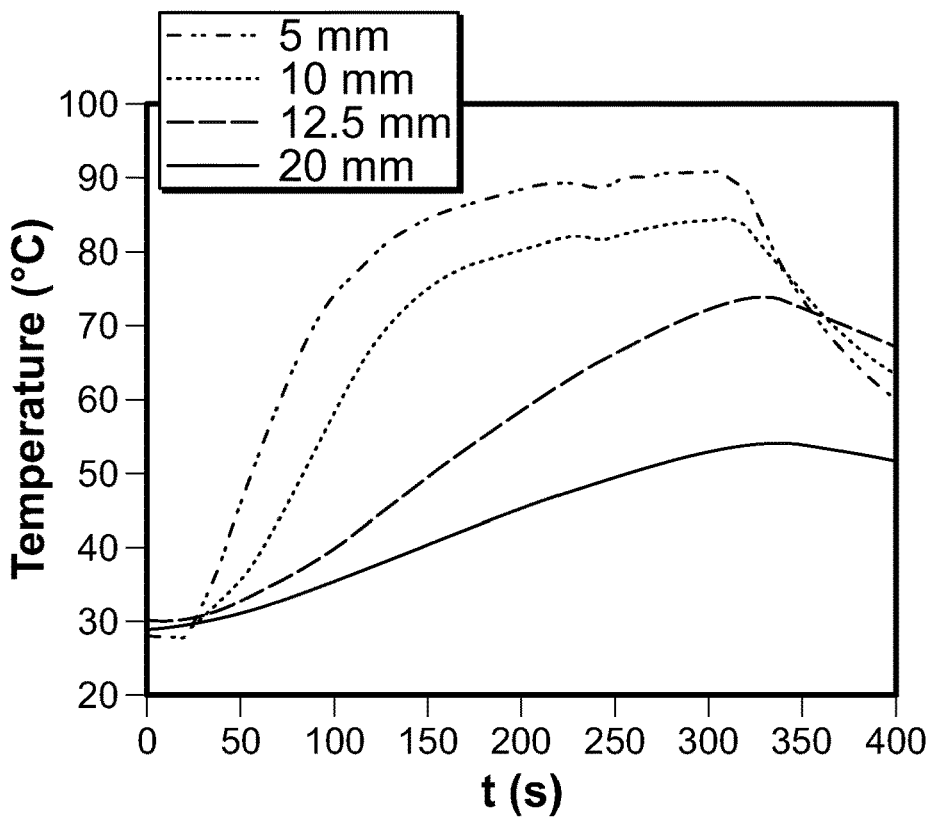

Despite the variability in ablating the lung tissue, we observed that the application of microwave energy raised lung tissue to ablative temperatures. As stated above, we measured temperatures using four probes spaced apart from one another. The temperatures measured at each probe are set forth in FIGS. 16-17. Particularly FIG. 16 shows the application of 60 W will raise lung tissue 1 cm radially from the applicator to temperatures near 60° C. in about 220 seconds. FIG. 17 shows the application of 80 W will cause the same effect in about half the time.

Example 4

In Vivo Canine Ablation

Another test of our MWA catheter was performed in vivo on a canine specimen. All ablations were performed under an experimental protocol approved by the local institutional animal care and use committee. Following induction of anesthesia, MWA applicators as described above were advanced to the target tissue via the working channel of a bronchoscope. Four ablations were performed, two in each lung, each at 60 W for 5 minutes.

Return loss measurements were recorded by the power meter during the procedures and ranged from −12.3 to −17.2 dB.

The primary objectives of this study were to verify proof-of-concept, safety, and containment of the ablation sites in the lung. Following ablation procedures, the animals were recovered from anesthesia and survived for 10 days. CT images were obtained at two days and ten days post procedure.

Figure 18:
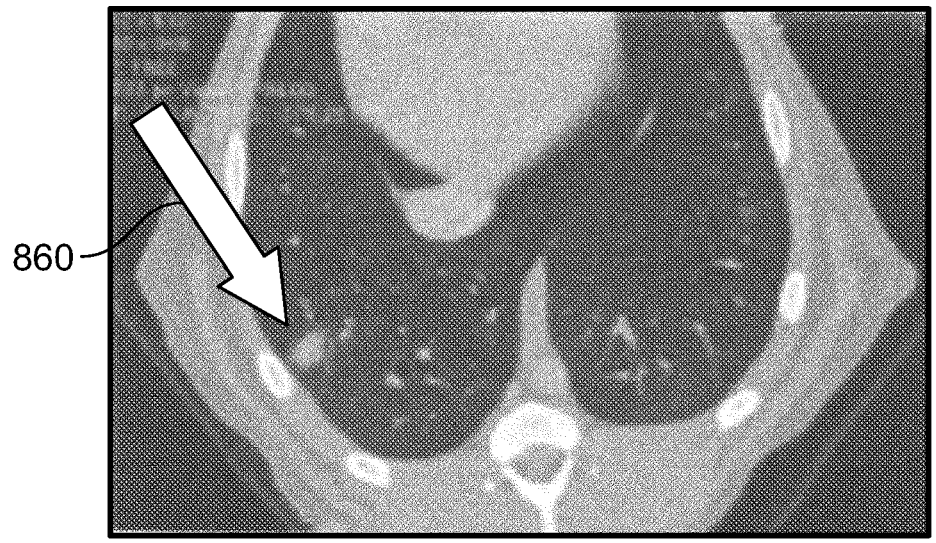
FIGS. 18-19 are in vivo canine lung ablation 10-day CT images.
Figure 19:
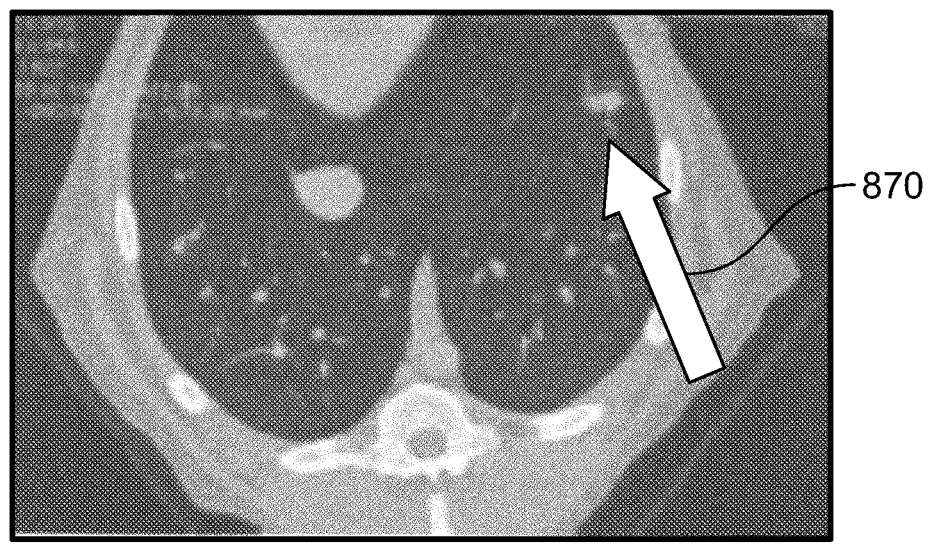

FIGS. 18-19 show the in vivo canine lung ablation 10-day CT images. Based on analysis of the CT data the estimated size of the ablation zones 860, 870 are given in Table 3 below.

TABLE 3

In vivo ablation results

| | | 2-day CT | | 10-day CT | |
|---|---|---|---|---|---|
| Power (W) | Duration (min) | Minor (mm) | Major (mm) | Minor (mm) | Major (mm) |
| 60 | 5 | 18 | 37 | 5 | 17 |
| 60 | 5 | 16 | 22 | 4 | 19 |
| 60 | 5 | 17 | 42 | 5 | 20 |
| 60 | 5 | 13 | 50 | 4 | 25 |
| Mean | | 16 | 37.75 | 4.5 | 20.25 |
| Std. dev. | | 2.2 | 11.8 | 0.6 | 3.4 |

The results of the in-vivo study showed that our prototype flexible MWA applicator was able to generate contained ablation zone in the lung tissue safely. No adverse effects were observed after the ablations were completed. Microwave ablation of lung tumors with a flexible bronchoscopic device offers a minimally invasive procedure and alternative to non-surgical candidates. We were able to overcome the challenges in the design and construction with significant engineering tradeoffs.

Our pilot in vivo experiment demonstrated the safety and containment of microwave energy within living lung tissue. Though embodiments of the present invention are described in connection with treatment of the lung, the present invention is not so limited. The invention is also intended for use in other minimally invasive endoscopic procedures.

Alternative Embodiments

Other modifications and variations can be made to the disclosed embodiments without departing from the subject invention.

For example, embodiments of the invention include other types of antennas including but not limited to: dipole, helical, slot, multiple slot, and monopole type antennas.

Figure 3B:
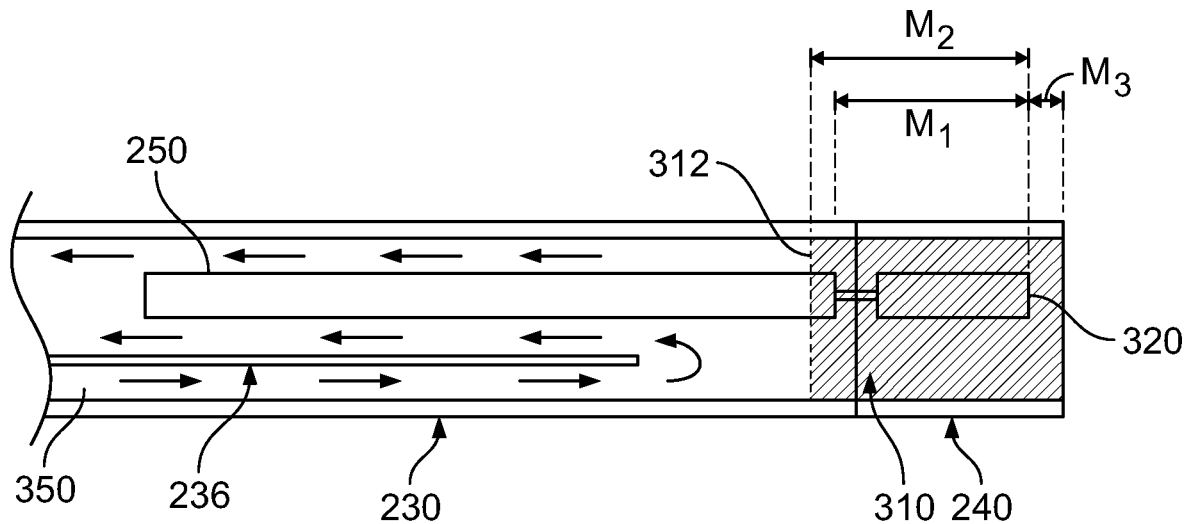
FIG. 3B is an axial sectional view of the distal section of the catheter shown in FIG. 2 according to another embodiment of the invention.

An example of a dipole-type antenna is shown in FIG. 3B. The antenna tip 320 may be fully or partially encapsulated by the epoxy 310 to prohibit the liquid from attenuating the microwaves intended to travel to the target tissue. In other embodiments, the antenna is not encapsulated.

The antenna tip 320 is spaced from the transmission line a distance $M_1$. The distance $M_1$ can be based on the electromagnetic wavelength, which is a function of frequency and the electrical properties of surrounding materials. At a frequency of 2.45 GHz, for example, $M_1$ can range from 4-14 mm. The liquid barrier 312 is spaced a distance $M_2$ from the tip of the antenna 320 and the tubular body portion 240 extends a distance $M_3$ beyond or distal to the tip of the antenna 320 thereby fully encapsulating the antenna. In embodiments, $M_2$ can range from 7-14 mm and $M_3$ can range from 0.5-3 mm. Otherwise, the catheter shown in FIG. 3B operates similar to the catheter shown in FIG. 3A, discussed above.

Embodiments of the invention can optionally include a spine element to compensate for "set" of the applicator, as well as to increase pushability of the applicator through the narrow passageways of the scope and patient. The spine element such as a nitinol member (or other suitable material) may be inserted in one lumen of the catheter. The configuration of the spine element may vary. Exemplary spine elements include but are not limited to a wire, tube, layer, or braided arrangement.

The distal tip of the applicator is generally shown having an atraumatic shape, however, the invention is not so limited. The distal tip of the applicators herein may be sharp, pointed, beveled, rounded, or tapered to facilitate tissue dissection and penetration.

In embodiments the antenna is not encapsulated whatsoever by the epoxy or liquid barrier described herein. Embodiments of the invention include fully cooled antenna designs.

Embodiments of the invention can optionally be used in connection with sensing or imaging equipment configured to give real-time feedback to the physician conducting a procedure. In embodiments, the novel flexible microwave applicator is integrated with a bronchoscopic imaging and software guidance platform to expand the use of the MWA as a treatment option for small (<2 cm) pulmonary tumors. This would allow physicians an even less invasive, immediate treatment option for lung tumors identified within the scope of current medical procedures, improve applicator placement accuracy and may increase efficacy while minimizing the risk of procedural complications.

In embodiments, the sensing or imaging equipment can give the physician information regarding the ablation boundary associated with the use of the device. If the ablation boundary does not extend to the edge of the desired target, the physician can reposition or rotate the device to treat the full extent of tissue in between the desired margins. For example, the device can be fabricated from MRI-compatible materials for use under MRI guidance. Such devices do not generate a visible imaging artifact when introduced into an MRI bore. Use of a device with an MRI offers the benefit of real-time volumetric temperature imaging for feedback controlled procedures. For instance, when targeting structures in very close proximity to several critical structures, MRI temperature imaging could be used to assess when the treatment boundary extended to the edge of the desired target, and then guide rotation of the device to target tissue in another direction Embodiments of the invention can optionally be used with a wide range of instruments including but not limited to a bronchoscope, endoscope, colonoscope, etc. The devices described herein can be applied to target tissues in regions that can be accessed percutaneously, endoluminally (e.g., bronchii, urethra, rectum, stomach, esophagus) or endovascularly (e.g., renal nerves). The device may also be used for moderate heating of tissues (e.g., between about 41 and 44 degrees Celsius) as an adjuvant to radiation and or chemotherapy for treatment of select cancers.

Other modifications and variations can be made to the disclosed embodiments without departing from the subject invention.

The invention claimed is:

1. A microwave ablation system for ablating a target tissue in a patient comprising:
    a microwave power source for generating microwave energy; and
    a microwave ablation catheter comprising:
    an elongate tubular body comprising a flexible proximal section, a distal section, and an open distal end;
    an antenna disposed within the distal section, and comprising a distal tip;
    a transmission line in electrical communication with the microwave power source and extending through the elongate tubular body to the antenna and for transmitting the microwave energy between the microwave power source and the antenna; and wherein the transmission line comprises a coaxial cable comprising an inner conductor and an outer conductor;
    a liquid inflow passageway and a liquid outflow passageway for transporting a liquid through the elongate tubular body to and from the distal section of the microwave ablation catheter, and wherein the liquid inflow passageway and liquid outflow passageway are thermally conductive such that heat is absorbed by the liquid as the liquid is circulated therethrough; and
    wherein the distal section of the microwave ablation catheter comprises a cylindrical plug comprising a low-loss dielectric material encapsulating the distal tip of the antenna, the cylindrical plug contacting inner walls of the distal section of the elongate tubular body forming a liquid barrier, prohibiting the liquid from passing therethrough, such that the liquid absorbs a first amount of the microwave energy emitted from the antenna when the microwave energy is transmitted to the antenna from the microwave power source and the liquid is circulated through the microwave ablation catheter; and wherein the distal section comprises a liquid flowpath that includes an exposed portion of the inner conductor for the liquid to make direct contact with the inner conductor of the coaxial cable of the transmission line; and wherein the liquid barrier is arranged within the distal section to prohibit the liquid from contacting the distal tip of the antenna.

2. The microwave ablation system of claim 1, wherein the inner conductor is electrically insulated from the outer conductor.

3. The microwave ablation system of claim 2, wherein the inner conductor comprises a braided center conductor and the outer conductor comprises a braided outer conductor.

4. The microwave ablation system of claim 3, wherein the antenna is selected from the group consisting of a dipole, helical, slot, multiple slot, and a monopole-type antenna.

5. The microwave ablation system of claim 4, wherein the antenna is an exposed portion of the inner conductor extending beyond the outer conductor.

6. The microwave ablation system of claim 1, wherein the microwave ablation catheter further comprises a cable which is adapted to detachably couple to a connector of the microwave power source.

7. The microwave ablation system of claim 1, wherein the antenna is reflector-less such that microwave energy is radiated spherically uniformly from the antenna.

8. The microwave ablation system of claim 1, wherein the liquid barrier is spaced 3-9 mm from the distal tip of the antenna.

9. The microwave ablation system of claim 1, wherein the microwave power source is configured to supply microwave energy for 2-15 minutes, at a frequency between 2.0 and 2.5 GHZ.

10. The microwave ablation system of claim 1, wherein the antenna is balun-less.

11. The microwave ablation system of claim 1, wherein the antenna and liquid barrier are arranged such that a ratio of total surface area of the antenna encapsulated to total surface area of the antenna is from 0.125 to 1.

12. The microwave ablation system of claim 1, wherein the liquid inflow passageway and the liquid outflow passageway are arranged outside of the transmission line.

13. The microwave ablation system of claim 1, wherein the coaxial cable further comprises an outer jacket, and wherein a portion of the outer jacket is removed defining said exposed portion of the inner conductor for the liquid to make direct contact with the inner conductor.

14. A microwave ablation catheter for ablating a target tissue in a patient comprising:
a flexible elongate tubular body comprising a proximal section, a distal section, and an open distal end;
an antenna disposed within the distal section, and comprising a distal tip;
a transmission line extending through the flexible elongate tubular body to the antenna, and for transmitting microwave energy from a microwave power source to the antenna; and wherein the transmission line comprises a coaxial cable comprising an inner conductor and an outer conductor;
a liquid inflow passageway and a liquid outflow passageway for transporting a liquid through the flexible elongate tubular body to and from the distal section of the microwave ablation catheter, and wherein the liquid inflow passageway and liquid outflow passageway are thermally conductive such that heat is absorbed by the liquid as the liquid is circulated therethrough; and
wherein the distal section of the microwave ablation catheter comprises a cylindrically shaped low-loss dielectric material encapsulating the distal tip of the antenna, the cylindrically shaped low-loss dielectric material contacting inner walls of the distal section of the flexible elongate tubular body forming a liquid barrier, prohibiting the liquid from passing therethrough and reaching the distal tip of the antenna, such that the liquid absorbs a first amount of the microwave energy emitted from the antenna in a proximal direction when the microwave energy is transmitted to the antenna from the microwave power source and the liquid is circulated through the microwave ablation catheter; and
wherein the distal section comprises a liquid flowpath that includes an exposed portion of the inner conductor for the liquid to make direct contact with the inner conductor of the coaxial cable of the transmission line.

15. The microwave ablation catheter of claim 14, wherein the inner conductor is electrically insulated from the outer conductor.

16. The microwave ablation catheter of claim 15, wherein the inner conductor comprises a braided center conductor and the outer conductor comprises a braided outer conductor.

17. The microwave ablation catheter of claim 14, wherein the antenna is reflector-less such that microwave energy is radiated omnidirectionally from antenna.

18. The microwave ablation catheter of claim 14, further comprising a cable extending from a proximal end of the flexible elongate tubular body, and the cable comprising a hub adapted to detachably couple to the microwave power source.

19. The microwave ablation catheter of claim 14, wherein the flexible elongate tubular body has a shape and flexibility to be advanced through an endoscope during an endoscopic procedure.

20. The microwave ablation catheter of claim 14, wherein the liquid barrier is spaced 3-9 mm from the distal tip of the antenna.

* * * * *